(12) United States Patent
Rieping

(10) Patent No.: US 11,053,526 B2
(45) Date of Patent: Jul. 6, 2021

(54) PROCESS FOR PREPARING L AMINO ACIDS USING IMPROVED STRAINS OF THE ENTEROBACTERIACEAE FAMILY

(71) Applicant: EVONIK OPERATIONS GMBH, Essen (DE)

(72) Inventor: Mechthild Rieping, Bielefeld (DE)

(73) Assignee: Evonik Operations GmbH, Essen (DE)

( * ) Notice: Subject to any disclaimer, the term of this patent is extended or adjusted under 35 U.S.C. 154(b) by 65 days.

(21) Appl. No.: 16/533,841

(22) Filed: Aug. 7, 2019

(65) Prior Publication Data

US 2020/0080118 A1 Mar. 12, 2020

(30) Foreign Application Priority Data

Aug. 9, 2018 (EP) .................................. 18188250
Sep. 4, 2018 (CN) ......................... 201811024315.4

(51) Int. Cl.
| | | |
|---|---|---|
| C12P 13/24 | (2006.01) | |
| C12P 13/08 | (2006.01) | |
| C12P 13/06 | (2006.01) | |
| C12P 13/22 | (2006.01) | |
| A23L 33/175 | (2016.01) | |
| A23K 20/142 | (2016.01) | |
| A23K 10/12 | (2016.01) | |

(52) U.S. Cl.
CPC ............... *C12P 13/24* (2013.01); *C12P 13/06* (2013.01); *C12P 13/08* (2013.01); *C12P 13/227* (2013.01); *A23K 20/142* (2016.05); *A23L 33/175* (2016.08); *A23V 2002/00* (2013.01)

(58) Field of Classification Search
None
See application file for complete search history.

(56) References Cited

U.S. PATENT DOCUMENTS

| | | |
|---|---|---|
| 4,278,765 A | 7/1981 | Debabov et al. |
| 4,321,325 A | 3/1982 | Debabov et al. |
| 4,371,614 A | 2/1983 | Anderson et al. |
| 5,175,107 A | 12/1992 | Debabov et al. |
| 5,631,157 A | 5/1997 | Debabov et al. |
| 5,756,345 A | 5/1998 | Camakaris et al. |
| 5,763,230 A | 6/1998 | De Hollander et al. |
| 5,939,295 A | 8/1999 | Dunkak et al. |
| 6,180,373 B1 | 1/2001 | Wich et al. |
| 6,319,696 B1 | 11/2001 | Kishino et al. |
| 6,562,601 B2 | 5/2003 | Hermann et al. |
| 6,630,332 B2 | 10/2003 | Rieping et al. |
| 7,094,584 B2 | 8/2006 | Kreutzer et al. |
| 7,211,415 B2 | 5/2007 | Rieping et al. |
| 7,241,600 B2 | 7/2007 | Rieping et al. |
| 7,319,026 B2 | 1/2008 | Rieping et al. |
| 7,575,905 B2 | 8/2009 | Rieping et al. |
| 7,638,313 B2 | 12/2009 | Rieping et al. |
| 7,759,094 B2 | 7/2010 | Rieping et al. |
| 8,143,032 B1 | 3/2012 | Rieping et al. |
| 8,945,907 B2 | 2/2015 | Ju |
| 9,394,346 B2 | 7/2016 | Livshits et al. |
| 9,587,261 B2 | 3/2017 | Lee et al. |
| 2006/0211095 A1 | 9/2006 | Schlosser |
| 2009/0258401 A1 | 10/2009 | Iyo |
| 2017/0218385 A1 | 8/2017 | Hayes |
| 2017/0360963 A1 | 12/2017 | Haining |
| 2020/0216867 A1 | 7/2020 | Rieping |

FOREIGN PATENT DOCUMENTS

| | | |
|---|---|---|
| CA | 1 182 409 | 2/1985 |
| DE | 10 2004 028 859 | 2/2005 |
| EP | 0 301 572 | 2/1989 |
| EP | 1 013 765 | 6/2000 |
| WO | WO 87/01130 | 2/1987 |
| WO | WO 98/04715 | 2/1998 |
| WO | WO 00/09660 | 2/2000 |
| WO | WO 00/09661 | 2/2000 |
| WO | WO 01/14525 | 3/2001 |
| WO | WO 02/18543 | 3/2002 |
| WO | WO 02/26993 | 4/2002 |
| WO | WO 02/29080 | 4/2002 |
| WO | WO 2005/014840 | 2/2005 |
| WO | WO 2005/014841 | 2/2005 |
| WO | WO 2005/014842 | 2/2005 |
| WO | WO 2007/069782 | 6/2007 |
| WO | WO 2007/086618 | 8/2007 |

OTHER PUBLICATIONS

Aleshin, et al.,"A new family of amino-acid-efflux proteins," *TIBS* 24(4):133-135 (Apr. 1999).
Blattner, et al., "The Complete Genome Sequence of *Eschericha coli* K-12," *Science* 277:1453-1462 (Sep. 1997) with Figure 3: map of *Eschericha coli* sequence attached.
Chapon, "Expression of malT, the regulator gene of the maltose regulon in *Eschericha coli*, is limited both at transcription and translation," *The EMBO Journal* 1(3):369-374 (1982).
Debabov, "The Threonine Story," *Advances in Biochemical Engineering* 79:113-136 (2003).
Fournier, et al., "Point Mutation in the Pribnow Box, the Molecular Basis of β-Lactamase Overproduction in *Klebsiella oxytoca*," *Antimicrobial Agents and Chemotherapy* 39(6):1365-1368 (Jun. 1995).
Harley, et al., "Analysis of *E. coli* promoter sequences," *Nucleic Acids Research* 15(5):2343-2361 (1987).

(Continued)

*Primary Examiner* — Suzanne M Noakes
*Assistant Examiner* — Jae W Lee
(74) *Attorney, Agent, or Firm* — Law Office of: Michael A. Sanzo, LLC

(57) ABSTRACT

The invention relates to a recombinant, L-amino acid-secreting microorganism of the Enterobacteriaceae family, comprising an DNA fragment having promoter activity that is functionally linked to a polynucleotide coding for a membrane protein, characterized in that the DNA fragment having promoter activity comprises the SEQ ID NO: 8.

16 Claims, 2 Drawing Sheets

Specification includes a Sequence Listing.

(56) References Cited

OTHER PUBLICATIONS

Hawley, et al., "Composition and analysis of *Eschericha coli* promoter DNA sequences," *Nucleic Acids Research* 11(8):2237-2255 (1983).
Horton, "PCR-Mediated Recombination and Mutagensis," *Molecular Biotechnology* 3:93-98 (Apr. 1995).
Komatsubara, et al., "Transductional Construction of a Threonine-Producing Strain of *Serratia marcescens*," *Applied and Environmental Microbiology* 38(6):1045-1051 (Dec. 1979).
Kruse, et al., "Influence of threonine exporters on threonine production in *Eschericha coli*," *Appl. Microbiol. Biotechnol.* 59(2-3):205-210 (2002).
Link, et al., "Methods for Generating Precise Deletions and Insertions in the Genome of Wild-Type *Eschericha coli*: Application to Open Reading Frame Characterization," *Journal of Bacteriology* 179(20):6228-6237 Oct. 1997).
Masuda, et al., "Improvement of Nitrogen Supply for L-Threonine Production by a Recombinant Strain of *Serratia marcescens*," *Applied Biochemistry and Biotechnology* 37(3):255-265 (1992).
Okamoto, et al., "Hyperproduction of L-Threonine by an *Eschericha coli* Mutant with Impaired L-Threonine Uptake," *Biosci. Biotech. Biochem.* 61(11):1877-1882 (Jun. 1997).
Rieping and Hermann, "L-Threonine," *Microbiology Monographs* 5:71-79, Springer Verlag Berlin / Heidelberg (2007).
Rosenberg, et al., "The relationship between function and DNA sequence in an intercistronic regulatory region in phage λ," *Nature* 272:414-423 (Mar. 1978).
Smith, et al., "Amplification and Modification of Dihydrofolate Reductase in *Eschericha coli*," *The Journal of Biological Chemistry* 257(15):9043-9048 (Aug. 1982).
Sugita, et al., "Cloning and characterization of the mutated threonine operon (thr $A_1 5A_2 5BC$) of *Serratia marcescens*," *Gene* 57(2-3):(1987).
Travers, "Conserved features of coordinately regulated *E. coli* promoters," *Nucleic Acids Research* 12(6):2605-2618 (1984).
Zakataeva, et al., "The novel transmenbrane *Eschericha coli* proteins involved in the amino acid efflux," *FEBS Letters* 452(3):228-232 (1999).
NCBI Accession No. NC_000913; *E. coli* strain K12 substr. MG1655, rhtC nucleotide and protein sequence, first submitted in 1997 and subsequently revised.
UniProtKB accession No. P0AG38; *E. coli* strain K12, rhtC protein sequence, last modified Dec. 20, 2005.
UniProtKB accession No. A0A2U8YHF1, *E. coli* 0145 RhtC protein sequence, last modified Sep. 12, 2018.
NCBI accession No. NC_000913, *E. coli* K12 substr. MG1655 genome sequence from nucleotide 4005780 to 4006400; first deposited in 1997 and subsequently revised.
NCBI accession No. NC_003198, *Salmonella enterica* subsp. *enterica serovar* Typhi str. CT18; rhtC gene and protein sequence, submitted Oct. 2001.
NCBI accession No. NC_000913, *E. coli* K-12 substr. MG1655, genome sequence from nucleotide 4005280 to 4006600; deposited 2005-2006.
UniProtKB accession No. A0A349FSM4, *Shigella* sp., RhtC protein sequence, last modified Nov. 7, 2018.
NCBI accession No. NC_004547.2, *Erwina carotovora* subsp. *atroseptica* SCR11043, RhtC gene and protein sequence, Jul. 9, 2004.
GenBank No. CP000266, *Shigella flexneri* 5 str. 8401, yigJ protein sequence, Jan. 2014.
GenBank No. CP000034, *Shigella dysenteriae* Sd197, yigJ protein sequence, Oct. 29, 2004.
GenBank No. CP000036, *Shigella boydii* yigJ protein sequence, Oct. 29, 2004.
GenBank No. CP000038, *Shigella sonnei* Ss046, yigJ protein sequence, Oct. 29, 2004.
GenBank No. AE006468.2, *Salmonella enterica* subsp. *enterica serovar Typhimurium* str LT2, RhtC protein sequence, Jan. 13, 2016.
European Search Report and Search Opinion for corresponding European application, EP 18 18 8250 completed Sep. 18, 2018.
Brewster, et al., "Tuning Promoter Strength through RNA Polymerase Binding Site Design in *Escherichia coli*," *PLOS Computational Biology* 8(12):e1002811 pp. 1-10 (Dec. 2012).
AroP gene in *E. Coli* strain K12 substrate MG1655; Ncbi Reference Sequence NC-000913.3 retrieved on Mar. 29, 2020.
MdfA gene in *E. Coli* strain K12 substrate MG1655; NCBI Reference Sequence NC-000913.3 retrieved on Mar. 29, 2020.
Mtr gene in *E. Coli* strain K12 substrate MG1655; NCBI Reference Sequence NC-000913.3 retrieved on Mar. 29, 2020.
Chung, et al., "One-step preparation of competent *Escherichia coli*: Transformation and storage of bacterial cells in the same solution," *Proc. Natl. Acad. Sci. USA* 86(7):2172-2175 (Apr. 1989).
Cohen, et al., "Revised Interprepation of the Orgin of the pSC101 Plasmid," *Journal of Bacteriology* 132(2):734-737 (Nov. 1977).
Hui, et al., "Mutagensis of the three bases preceding the start codon of the β-galactosidase mRNA and its effect on translation in *Escherichia coli*," *The EMBO Journal* 3(3):623-629 (Mar. 1984).
Lewinson, et al., "The *Escherichia coli* multidrug transporter MdfA catalyzes both electrogenic and electroneutral transport reactions," *Proc. Natl. Acad. Sci. USA* 100(4):1667-1672 (Feb. 2003).
Stenström, et al., "Cooperative effects by the initiation codon and its flanking regions on translation initiation," *Gene* 273(2):259-265 (Aug. 2001).
U.S. Appl. No. 16/734,362, filed Jan. 5, 2020, Rieping.
GenBank Accession No. AAC73929, www.ncbi.nim.nih.gov (2014).
Uniprot, Accession No. P0AEY8, www.uniprot.org (2017).
Court, et al., "Genetic Engineering Using Homologous Recombination[1]," *Annu. Rev. Genet.* 36:361-388 (2002).
Mahr, et al., "Screening of an *Escherichia coli* promoter library for a phenylalanine biosensor," *Appl. Microbiol. Biotechnol.* 100:6739-6753 (2016).
Nagarathinam, et al., "The multidrug-resistance transporter MdfA from *Escherichia coli*: crystallization and X-ray diffraction analysis," *Acta. Cryst.*F73:423-430 (2017).
Wahl, et al., "Molecular Hybridization of Immobilized Nucleic Acids: Theoretical Concepts and Practical Considerations," *Methods in Enzymology* 152:399-407 (1987).
Weickert, et al., "Optimization of heterologous protein production in *Escherichia coli*," *Current Opin. Biotechnol.* 7:494-499 (1996).

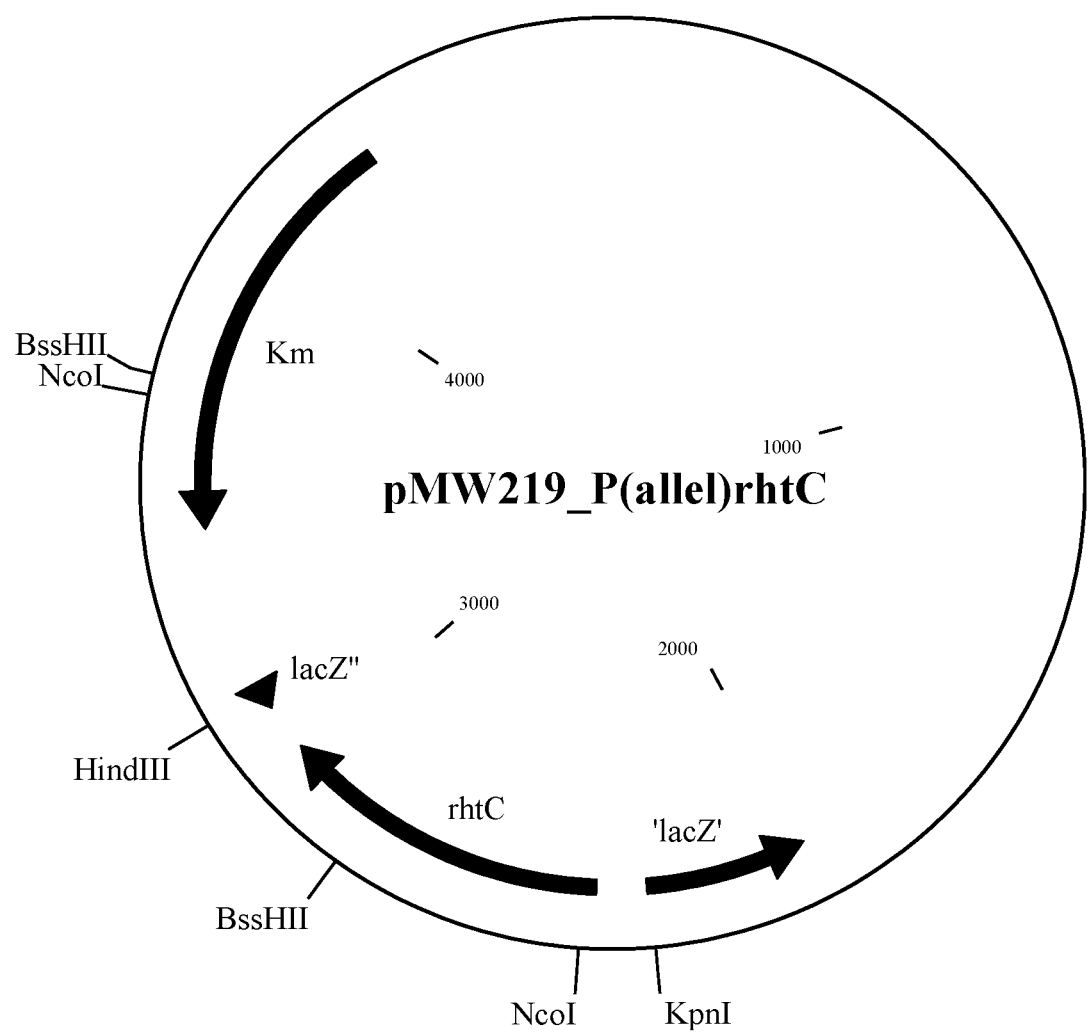
Figure 1: Map of expression plasmid pMW219_P(allel)rhtC

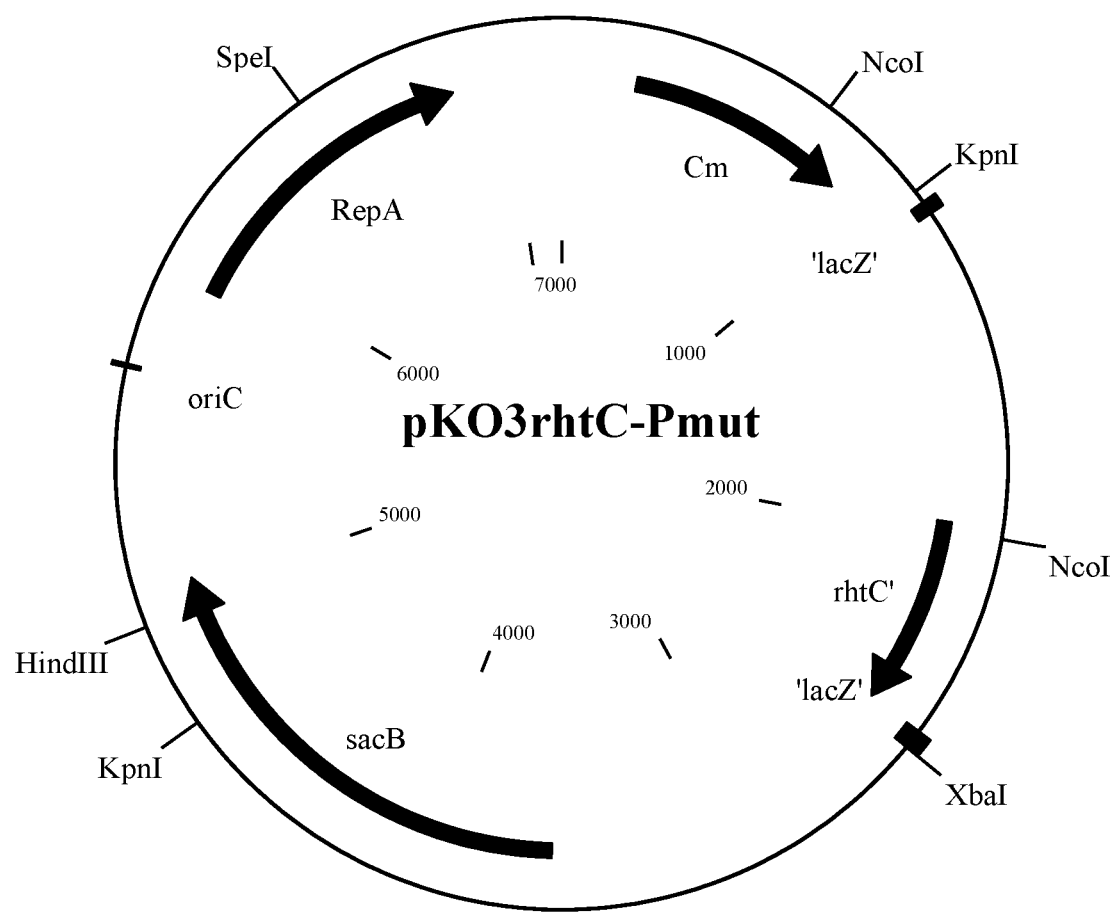
Figure 2: Map of gene replacement vector pKO3rhtC-Pmut

PROCESS FOR PREPARING L AMINO ACIDS USING IMPROVED STRAINS OF THE ENTEROBACTERIACEAE FAMILY

CROSS REFERENCE TO RELATED APPLICATIONS

The present application claims priority under 35 USC § 119 to European application, EP 18188250.7, filed on Aug. 9, 2018, and to Chinese application CN 201811024315.4, the contents of which is incorporated herein by reference in its entirety.

FIELD OF THE INVENTION

The present invention relates to a process for fermentatively preparing L-amino acids such as L-threonine using a recombinant microorganism of the Enterobacteriaceae family, which comprises a specific DNA fragment having promoter activity that is functionally linked to a polynucleotide coding for a membrane protein or of an amino acid transporter, and to the respective microorganisms.

BACKGROUND OF THE INVENTION

L-amino acids, in particular L-threonine, L-homoserine, L-histidine, L-lysine, L-tryptophan, L-valine, L-leucine, and L-isoleucine are used in human medicine and in the pharmaceutical industry, in the foodstuff industry and in animal nutrition.

It is known that L-amino acids are prepared by fermenting Enterobacteriaceae strains, in particular *Escherichia coli* (*E. coli*) and *Serratia marcescens*. Because of the great importance, efforts are continually being made to improve the preparation processes. Methodological improvements may concern measures relating to fermentation technology, such as, for example, stirring and oxygen supply, or the composition of the nutrient media, such as, for example, selection of the sugar used or the sugar concentration during the fermentation, or the working-up to the product form, for example by means of ion exchange chromatography, or the intrinsic performance properties of the microorganism itself.

In wild-type strains, strict regulatory mechanisms prevent metabolic products such as amino acids from being produced in excess of what is needed by said strains and from being released into the medium. The construction of amino acid-overproducing strains therefore requires, from a manufacturers point of view, these metabolic regulations to be overcome.

Methods of mutagenesis, selection and mutant choice are used for removing said control mechanisms and improving the performance properties of these microorganisms. This results in strains which are resistant to antimetabolites such as, for example, the threonine analog α-amino-β-hydroxyvaleric acid (AHV), or are auxotrophic for metabolites of regulatory importance and produce L-amino acids such as, for example, L-threonine. For example, a strain producing L-isoleucine is characterized by resistance to the isoleucine analog thiaisoleucine.

For a number of years now, recombinant DNA methods have likewise been used for improving in a specific manner L-amino acid-producing strains of the Enterobacteriaceae family by amplifying, for example, individual amino acid biosynthesis genes or altering the properties of special genes and investigating the effect on production. Comparative information on the cell biology and molecular biology of *Escherichia coli* and *Salmonella* can be found in Neidhardt (ed): *Escherichia coli* and *Salmonella*, Cellular and Molecular Biology, $2^{nd}$ edition, ASM Press, Washington, D.C., USA, (1996). A review on the metabolism and production of L-threonine has been published by Debabov (Advances in Biochemical Engineering Vol. 79, 113-136 (2003)) and Rieping and Hermann (Microbiology Monographs, Vol. 5, 71-92, ISSN 1862-5576 (print) and 1862-5584 (online), Springer Verlag Berlin/Heidelberg (2007)).

The protein having the activity of an amino acid exporter (gene product of the rhtC-gene) has previously been found to catalyze the export of the amino acid L-threonine. Thus, overexpression of rhtC results in external accumulation of this metabolite by mediating a resistance to threonine (Zakataeva et al., FEBS Letters 452(3):228-32 (1999), Kruse et al., Applied Microbiological Biotechnology 59(2-3):205-10 (2002)). The amino acid exporter belongs to the Rht family of amino acid exporters (Aleshin et al., Trends in Biochemical Science 24(4):133-5 (1999)), and is assumed to have the function of a threonine/proton antiporter.

The nucleotide sequence of the wild form of the rhtC gene coding for the *Escherichia coli* amino acid exporter and of the upstream region is generally accessible in the database of the National Center for Biotechnology Information (NCBI) of the National Library of Medicine (Bethesda, Md., USA) under accession number NC000913 (region: 4005780-4006400 and upstream).

European Patent Application EP 1 013 765 A1 describes the beneficial effect of rhtC gene overexpression on the production and preparation of various amino acids such as L-threonine, L-homoserine, L-valine and L-leucine by strains of the genus *Escherichia*, said overexpression being achieved in this case by increasing the copy number of the rhtC gene or by coupling the rhtC gene to a promoter efficient in *Escherichia*.

The present inventors recently found that—depending on the expression system—a high expression level for membrane proteins, such as amino acid transporters and in particular amino acid exporters like rhtC, may result in a decreased production level of the desired amino acid. In particular and with regard to amino acid yields, strong promoter systems are not suitable for expressing the aforementioned membrane proteins in the respective amino acid production systems.

Accordingly, for membrane proteins it is particularly important to adjust the correct level of (constitutive or inducible) expression during the fermentation process when high concentrations of the amino acids accumulate in the fermentation broth. EP 1 013 765 describes a method of making a bacterium L-threonine resistant by amplifying a copy number of the rhtC gene and the L-threonine titer is increased relative to the strain in which the rhtC gene was not enhanced. However, the impact of overexpression in strains of the genus *Escherichia* producing commercial relevant volumes of the amino acid is not described.

Gene expression is controlled inter alia by the promoter region within the 5' region of a gene. The promoter initiates transcription by way of the interaction of transcription factors and RNA polymerase. As a result, promoters contain a number of conserved sequence motifs which can be determined on the basis of their consensus sequences (Fournier et al., Antimicrobial Agents and Chemotherapy 39(6):1365-1368 (1995); Chapon, EMBO Journal 1:369-374 (1982); Smith et al., Journal of Bacteriological Chemistry 257:9043-9048 (1982)).

The following general bacterial promoter elements were classified on the basis of consensus sequences for genes transcribed with the aid of the sigma-70 factor in the best studied bacterial model organism, *Escherichia coli* (Rosenberg et al., Nature 272:414-423 (1978); Hawley and McClure, Nucleic Acids Research 11(8):2237-2255 (1983)):

- the −35-region (sequence 35 base pairs upstream of the transcription initiation point), with the consensus sequence: 5'-TTGACA-3',
- the −10-region (this sequence can be found about 10 base pairs upstream of the transcription initiation point), also called Pribnow box, with the consensus sequence: 5'-TATAAT-3'.

The sigma factor of RNA polymerase binds to these two regions, and said polymerase then induces transcription of the downstream gene. "Consensus sequences" for strong and weak promoters can be derived from comparing the DNA sequences of individual promoters. The positions of the promoter elements with respect to each other and to the transcription initiation point are also important. The distance from the −10 region to the transcription initiation point in the consensus sequence is from 5 to 7 base pairs, with the −10 and −35 regions being separated by from 16 to 18 base pairs. However, the similarity of a promoter to the consensus sequence does not necessarily provide high expression levels in every strain of the genus *Escherichia* and other regulatory mechanisms to control expression levels might matter more than an optimized consensus sequence.

In view of the above findings with regard to the membrane protein expression levels, it was a remaining need to provide improved methods and tools for modulating the expression level of membrane proteins, in particular amino acid exporters such as rhtC in order to further improve the fermentative preparation of L-amino acids, in particular L-threonine, L-homoserine, L-lysine, L-tryptophan, L-valine, L-leucine, L-isoleucine and L-histidine, by means of L-amino acid-producing microorganisms of the Enterobacteriaceae family.

SUMMARY OF THE INVENTION

The present invention relates to a recombinant, L-amino acid-secreting microorganism of the Enterobacteriaceae family, comprising an DNA fragment having promoter activity that is functionally linked to a polynucleotide coding for a membrane protein, characterized in that the DNA fragment having promoter activity comprises SEQ ID NO: 8.

The present invention further provides a new method or process for preparing L-amino acids or feedstuff additives containing L-amino acids by using the aforementioned microorganism.

In addition, the invention pertains to a DNA fragment having promoter activity that comprises SEQ ID NO.:8, and that is functionally linked to a polynucleotide coding for a membrane protein.

Finally, the present invention relates to the use of the DNA fragment comprising SEQ IS NO.: 8 as a promoter for modulating the expression level of genes encoding membrane proteins or amino acid transporters.

DETAILED DESCRIPTION OF THE INVENTION

The present invention pertains to recombinant L-amino acid-secreting microorganisms of the Enterobacteriaceae family which comprise an DNA fragment having promoter activity being functionally linked to a polynucleotide coding for a membrane protein and which secrete, i.e. produce and concentrate in the cell or in the medium, an increased amount of L-amino acids, in particular L-threonine, L-homoserine, L-histidine, L-lysine, L-tryptophan, L-valine, L-leucine, and L-isoleucine, wherein the DNA fragment having promoter activity comprises SEQ ID NO: 8.

The polynucleotide according to SEQ ID NO.: 8 derives from the polynucleotide according to SEQ ID NO.: 7 (wt) by substitution of the nucleobase cytosine at position 24 by thymine.

The inventors have unexpectedly found that using the specific aforementioned promoter sequence enables the modulation of the expression level of genes coding for membrane proteins, in particular for amino acid transporters such as amino acid exporters like rhtC, in a way that improves the capacity of fermentative production of the amino acid when commercial relevant concentrations accumulate in the fermentation broth.

As used in the context of the present invention, the term "modulation of expression level" refers to setting a balanced expression level leading to an optimized yield of the amino acid product. As will be outlined in detail below, the gene expression level might be adapted to the specific needs of the abundance of transporter proteins in the cell membrane by using the aforementioned DNA fragments as promoter elements for regulating the expression level of genes encoding membrane proteins or amino acid transporters, in particular amino acid exporter genes such as rhtC in a high producer strain without affecting cellular fitness and production capacities.

The present invention further provides microorganisms which comprise an DNA fragment having promoter activity, characterized in that said DNA fragment is linked at the 3' end to a second DNA fragment carrying a ribosome binding site.

In microorganisms according to one embodiment of the present invention, the aforementioned DNA fragment may be linked at the 3' end to a second DNA fragment having the nucleotide sequence of positions 174 to 204 of SEQ ID NO: 9, which is the naturally occurring 3'-flanking region of the DNA fragment. Said second DNA fragment having the nucleotide sequence of positions 174 to 204 of SEQ ID NO: 9 may be linked at its 3' end to a polynucleotide coding for the membrane protein.

The membrane protein is preferably a protein having the activity of an amino acid transporter, in particular an amino acid exporter, such as rhtC.

The DNA fragment having promoter activity according to the present invention may be linked at the 5' end to a DNA fragment having the nucleotide sequence of positions 1 to 138 of SEQ ID NO: 9, which is the naturally occurring 5'-flanking region of the DNA fragment.

The microorganisms according to the present invention include in particular microorganisms of the Enterobacteriaceae family, in which a DNA fragment having promoter activity and comprising SEQ ID NO.: 8 is functionally linked at the 3' end to a polynucleotide whose amino acid sequence is at least 70% or at least 80%, or at least 90%, in particular at least 95%, preferably at least 98%, or at least 99%, particularly preferably up to 99.6%, and very particularly preferably up to 100%, identical to the amino acid sequence of SEQ ID NO: 2.

Said microorganisms comprise polynucleotides selected from the group consisting of:
a) polynucleotide having a nucleotide sequence selected from SEQ ID NO: 1 and nucleotide sequences complementary thereto;
b) polynucleotide having a nucleotide sequence corresponding to SEQ ID NO: 1 in the context of the degeneration of the genetic code;

c) polynucleotide sequence having a sequence which hybridizes with the sequence complementary to the sequence SEQ ID NO: 1 under stringent conditions, said stringent conditions being preferably achieved by a washing step in which the temperature is within a range from 64° C. to 68° C. and the salt concentration of the buffer is within a range from 2×SSC to 0.1×SSC;

d) polynucleotide having a sequence SEQ ID NO: 1 which comprises functionally neutral sense mutants, preferably a polynucleotide having the nucleotide sequence of SEQ ID NO: 1, said polynucleotides coding for the amino acid exporter.

The amino acid exporting protein is preferably RhtC.

The DNA fragment having promoter activity may be present in the chromosome of the microorganism. Alternatively, it may be located on an extrachromosomal replicating vector.

Basically, there are two possibilities for the expression of genes. In continuous expression, the gene is continuously expressed by means of a constitutive promoter and the corresponding protein accumulates in the cell.

On the other hand, an inducible promoter may be used for induced gene expression. The expression of the target gene is induced, that is enabled, by an inducer. This method is used if the (over)expression has negative effects on the production organism. Causes of this can be a high loading of the metabolic resources during the growth phase. The result is slower growth and thus prolonged runtimes of the bioreactor and associated therewith an increase in the costs in the case of industrial production. Induced expression is also advantageous in the case of cytotoxic products. Here, autointoxication and the death of the cell occurs after the induction of expression. With regard to the economy of a production process, it is therefore attempted to subdivide the process into a growth phase and a production phase. In the growth phase, an as large as possible amount of biomass is produced and in the production phase, the target protein is then produced by induction of the promoter. In this way, a maximal yield can be obtained, whereby the process becomes noticeably more economical.

The invention also relates to a process for the fermentative preparation of L-amino acids, in particular L-threonine, L-homoserine, L-histidine, L-lysine, L-tryptophan, L-valine, L-leucine, and L-isoleucine using recombinant microorganisms of the Enterobacteriaceae family which secrete L-amino acids, in particular even prior to the use of the DNA fragment having promoter activity according to the invention, and in which at least one polynucleotide coding for a membrane protein or for a protein having the activity of an amino acid transporter such as an amino acid exporter like rhtC is functionally linked to said DNA fragment having promoter activity.

The process for preparing L-amino acids by fermentation of recombinant microorganisms according to the present invention comprises the following steps:

(i) fermentation of a microorganism according to the present invention in a medium;
(ii) enrichment of the L-amino acid in the fermentation medium and/or in the microbial cell; and optionally
(iii) isolation of the L-amino acid.

In addition, the invention pertains to a DNA fragment having promoter activity and comprising SEQ ID NO.:8 that is functionally linked to a polynucleotide coding for a membrane protein.

Such DNA fragment comprising SEQ IS NO.: 8 may be used as a promoter for modulating the expression level of genes encoding membrane proteins or amino acid transporters, in particular amino acid exporter genes such as rhtC.

If mutations are carried out in the regulatory sequence upstream of the start codon, attention must be paid to the functionality of these elements as a function of the sequence and of the distances to the start codon. The expression "functionally linked" used herein means that a regulatory sequence such as a promoter controls expression of a gene.

Microorganisms producing L-amino acids prior to the use according to the invention of the DNA fragment having promoter activity do not include here the wild-type strains and frequently used laboratory strains such as, inter alia, DH5α, DH5αmcr, W3110, MG1655, MC4100, Y1089, H560 and MM152.

If L-amino acids or amino acids are mentioned herein below, these refer to one or more amino acids including their salts, selected from the group consisting of L-asparagine, L-threonine, L-serine, L-glutamate, L-glycine, L-alanine, L-cysteine, L-valine, L-methionine, L-proline, L-isoleucine, L-leucine, L-tyrosine, L-phenylalanine, L-histidine, L-lysine, L-tryptophan, L-arginine, L-glutamine, L-aspartate and L-homoserine. Particular preference is given to L-threonine, L-homoserine, L-histidine, L-lysine, L-tryptophan, L-valine, L-leucine, and L-isoleucine.

The term "use of the DNA fragment having promoter activity" or "use of a DNA fragment comprising SEQ ID NO.: 8 as a promoter" in this connection describes the incorporation of the DNA fragment upstream of a structural gene to regulate transcription.

Substitutions in the DNA fragment having promoter activity, which are used in the microorganisms employed for the process according to the invention, may be generated by using inter alia methods of directed mutagenesis described in the prior art.

It is possible to use methods of site-directed mutagenesis using mutagenic oligonucleotides (T. A. Brown: Gentechnologie für Einsteiger [Genetic engineering for beginners], Spektrum Akademischer Verlag, Heidelberg, 1993) or the polymerase chain reaction (PCR), as described in the manual by Gait: Oligonucleotide synthesis: A Practical Approach (IRL Press, Oxford, U K, 1984) or by Newton and Graham (PCR, Spektrum Akademischer Verlag, Heidelberg, 1994). The mutations generated may be determined and checked by DNA sequencing, for example by the method of Sanger et al. (Proceedings of the National Academy of Science USA 74 (12): 5463-5467 (1977)).

To construct base substitutions in the promoter region of the polynucleotide coding for a protein having the activity of an amino acid exporter, the Q5 Site-Directed Mutagenesis Kit from New England Biolabs GmbH (Frankfurt, Germany) may be used, for example. In using these methods, the region described in the prior art of approx. 200 base pairs in the 5' region of the nucleotide sequence coding for a protein having the activity of an amino acid exporter is amplified, starting from total DNA of a wild-type strain, with the aid of the polymerase chain reaction (PCR), cloned into suitable plasmid vectors, and the DNA is then subjected to the mutagenesis process. The point mutations may already be obtained via PCR by means of "GeneSOEing" (Gene Splicing by Overlap Extension, Horton, Molecular Biotechnology 3: 93-98 (1995)).

Furthermore, the toxicity caused by high concentrations of amino acids and/or associated molecules enables screening and selection of spontaneous mutations in the promoter region by increasing the resistance level of the relevant strains.

The promoter mutations generated may be incorporated into suitable strains, for example by transformation and the process of gene or allele replacement.

A common method, described by Hamilton et al. (Journal of Bacteriology 174, 4617-4622 (1989)), is the method of allele replacement with the aid of a conditionally replicating pSC101 derivative, pMAK705, or with pKO3 (Link et al., Journal of Bacteriology 179: 6228-6237). Other methods described in the prior art, such as, for example, that of Martinez-Morales et al. (Journal of Bacteriology 1999, 7143-7148 (1999)) or that of Boyd et al. (Journal of Bacteriology 182, 842-847 (2000)) may likewise be utilized.

It is also possible to transfer the promoter mutations generated into various strains by conjugation or transduction.

Thus, the mutated DNA fragment having promoter activity can be integrated stably in the chromosome of the microorganisms, thereby enabling the downstream structural gene to be expressed constitutively.

The mutated DNA fragment having promoter activity may also be present on an extrachromosomal replicating vector, thereby enabling the resulting protein of the downstream structural gene on expression plasmids to be overproduced.

More detailed explanations of the concept of genetics and molecular biology can be found in known textbooks of genetics and molecular biology, such as, for example, the textbook by Birge (Bacterial and Bacteriophage Genetics, 4$^{th}$ ed., Springer Verlag, New York (USA), 2000) or the textbook by Berg, Tymoczko and Stryer (Biochemistry, 5$^{th}$ ed., Freeman and Company, New York (USA), 2002) or the manual by Sambrook et al. (Molekular Cloning, A Laboratory Manual, (3-Volume Set), Cold Spring Harbor Laboratory Press, Cold Spring Harbor (USA), 2001).

The concentration of the protein can be determined by 1- and 2-dimensional protein gel fractation and subsequent optical identification of the protein concentration in the gel, using appropriate evaluation software. A common method of preparing said protein gels and of identifying the proteins is the procedure described by Hermann et al. (Electrophoresis, 22:1712-23 (2001)). The protein concentration may likewise be determined by Western blot hybridization with an antibody specific to the protein to be detected (Sambrook et al., Molecular cloning: a laboratory manual. 2$^{nd}$ Ed. Cold Spring Harbor Laboratory Press, Cold Spring Harbor, N.Y., 1989) and subsequent optical evaluation using appropriate software for concentration determination (Lohaus and Meyer (1998) Biospektrum 5:32-39; Lottspeich, Angewandte Chemie 38: 2630-2647 (1999)).

Chemically, a gene or allele is a polynucleotide. An alternative term here is nucleic acid, in particular desoxyribonucleic acid.

In this context, a DNA fragment refers to a section of a nucleotide sequence, which does not code for a protein or polypeptide or ribonucleic acid.

The terms polypeptide and protein can be used interchangeably.

An open reading frame (ORF) refers to a section of a nucleotide sequence, which codes or may code for a protein or polypeptide or ribonucleic acid to which no function can be assigned according to the prior art. After assigning a function to the section of the nucleotide sequence in question, the latter is usually referred to as a gene. Alleles mean generally alternative forms of a given gene. Said forms are distinguished by differences in the nucleotide sequence.

A gene product refers usually to the protein or ribonucleic acid encoded by a nucleotide sequence, i.e. an ORF, a gene or an allele.

The microorganisms, in particular recombinant microorganisms, which comprise an DNA fragment having promoter activity comprising SEQ ID NO.: 8 that is functionally linked to a polynucleotide coding for a membrane protein or for a protein having the activity of an amino acid transporter such as an amino acid exporter like rhtC, and which are subject matter of the present invention can produce L-amino acids from glucose, sucrose, lactose, fructose, maltose, molasses, where appropriate starch, where appropriate cellulose, or from glycerol and ethanol, where appropriate also from mixtures.

The microorganisms according to the present inventions are representatives of the Enterobacteriaceae family. They may, for example, be selected from the genera *Escherichia, Erwinia, Providencia* and *Serratia*. Preference is given to the genera *Escherichia* and *Serratia*. Special mention should be made of the species *Escherichia coli* of the genus *Escherichia* and the species *Serratia marcescens* of the genus *Serratia*.

Recombinant microorganisms are usually generated by transformation, transduction or conjugation, or a combination of these methods, with a vector which comprises the desired gene, the desired ORF, an allele of said gene or ORFs or parts thereof and/or a promoter which enhances expression of said gene or ORFs.

To prepare the L-amino acid-concentrating strains of the Enterobacteriaceae family which comprise an DNA fragment having promoter activity comprising SEQ ID NO.: 8 that is functionally linked to a polynucleotide coding for a protein having the activity of an amino acid exporter, preference is given to using strains (starting strains or parent strains) which already have the ability to concentrate the desired L-amino acid in the cell and/or to secrete it into the surrounding nutrient medium or to accumulate it in the fermentation broth. The term "produce" may also be used here. More specifically, the strains employed for the inventive measures have the ability to concentrate or accumulate ≥(at least) 2.0 g/l, ≥8.0 g/l, ≥10.0 g/l, ≥50 g/l, ≥100 g/l or ≥150 g/l of L-amino acid in the cell and/or in the nutrient medium or the fermentation broth in ≤5 (no more than) 120 hours, ≤96 hours, ≤48 hours, ≤36 hours, ≤24 hours or ≤12 hours. Said strains may have been prepared by mutagenesis and selection, by recombinant DNA techniques or by a combination of both methods.

Said L-amino acid-secreting strains produce one or more, preferably one, or essentially one, amino acid selected from the group consisting of L-asparagine, L-threonine, L-serine, L-glutamate, L-glycine, L-alanine, L-cysteine, L-valine, L-methionine, L-proline, L-isoleucine, L-leucine, L-tyrosine, L-phenylalanine, L-histidine, L-lysine, L-tryptophan, L-arginine, L-glutamine, L-aspartate and L-homoserine, preferably selected from the group consisting of L-threonine, L-homoserine, L-histidine, L-lysine, L-tryptophan, L-valine, L-leucine, and L-isoleucine. The term L-amino acid or amino acid also comprises its salts.

The term "one or essentially one amino acid" takes into account that, in addition to the desired L-amino acid, one or more other amino acids of said L-amino acids (secondary amino acids) may be produced. The proportion of these secondary amino acids is ≥0 to no more than 40%, preferably ≥0 to no more than 20%, particularly preferably ≥0 to no more than 10% and very particularly preferably ≥0 to no more than 5%, based on the amount of the desired L-amino acid.

Strains which may be mentioned as examples of suitable parent strains, in particular strains producing or secreting L-threonine, of the genus *Escherichia*, in particular of the species *Escherichia coli*, are:

*Escherichia coli* H4581 (EP 0 301 572)
*Escherichia coli* KY10935 (Bioscience Biotechnology and Biochemistry 61(11): 1877-1882 (1997)
*Escherichia coli* VNIIgenetika MG442 (U.S. Pat. No. 4,278,765)
*Escherichia coli* VNIIgenetika M1 (U.S. Pat. No. 4,321, 325)
*Escherichia coli* VNIIgenetika 472T23 (U.S. Pat. No. 5,631,157)
*Escherichia coli* TH 14.97 (WO 02/26993)
*Escherichia coli* TH 21.97 (WO 02/26993)
*Escherichia coli* BKIIM B-3996 (U.S. Pat. No. 5,175, 107)
*Escherichia coli* BKIIM B-3996ΔtdhΔpckA/pVIC40 (WO 02/29080)
*Escherichia coli* kat 13 (WO 98/04715)
*Escherichia coli* Kat 69.9 (WO 02/26993)
*Escherichia coli* KCCM-10132 (WO 00/09660)
*Escherichia coli* KCCM-10168 (WO 01/14525)
*Escherichia coli* KCCM-10133 (WO 00/09661)

Examples which may be mentioned of suitable parent strains producing or secreting L-threonine, of the genus *Serratia*, in particular the species *Serratia marcescens*, are:

*Serratia marcescens* HNr21 (Applied and Environmental Microbiology 38(6): 1045-1051 (1979))
*Serratia marcescens* TLr156 (Gene 57(2-3): 151-158 (1987))
*Serratia marcescens* 1-2000 (Applied Biochemistry and Biotechnology 37(3): 255-265 (1992)).

L-threonine-producing or secreting strains of the Enterobacteriaceae family preferably have, inter alia, one or more of the genetic or phenotypical features selected from the group consisting of: resistance to α-amino-β-hydroxyvaleric acid, resistance to thialysine, resistance to ethionine, resistance to α-methylserine, resistance to diaminosuccinic acid, resistance to α-aminobutteric acid, resistance to borrelidine, resistance to cyclopentane-carboxylic acid, resistance to rifampicine, resistance to valine analogs such as, for example, valine hydroxamate, resistance to purine analogs such as, for example, 6-dimethylaminopurine, need for L-methionine, where appropriate partial or compensable need for L-isoleucine, need for meso-diaminopimelic acid, auxotrophy with regard to threonine-containing dipeptides, resistance to L-threonine, resistance to threonine-raffinate, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, where appropriate ability to utilize sucrose, enhancement of the threonine-operon, increase in homoserine dehydrogenase I-aspartate kinase I, preferably the feedback-resistant form, increase in homoserine kinase, increase in threonine synthase, increase in aspartate kinase, where appropriate the feedback resistant form, increase in aspartate semialdehyde dehydrogenase, increase in phosphoenol pyruvate carboxylase, where appropriate the feedback-resistant form, increase in phosphoenol pyruvate synthase, increase in transhydrogenase, increase in the RhtB gene product, increase in the YfiK gene product, increase in a pyruvate carboxylase, and attenuation of acetic acid formation.

An example which may be mentioned of a suitable parent strain which secretes or produces L-homoserine, of the genus *Escherichia*, in particular the species *Escherichia coli* is: *Escherichia coli* NZ10rhtA23/pAL4 (U.S. Pat. No. 6,960,455).

L-homoserine-producing or secreting strains of the Enterobacteriaceae family preferably have, inter alia, one or more of the genetic or phenotypical features selected from the group consisting of: need for L-threonine, need for L-methionine, need for L-isoleucine, a defective homoserine kinase, where appropriate ability to utilize sucrose, increase in homoserine dehydrogenase I/aspartate kinase I, preferably the feedback-resistant form, increase in the RhtA gene product.

Examples which may be mentioned of a suitable parent strain which secretes or produces L-lysine, of the genus *Escherichia*, in particular the species *Escherichia coli* are:

*Escherichia coli* VL613 (VKPM B-3423) (EP1149911)
*Escherichia coli* AJ11442 (FERM BP-1543) (U.S. Pat. No. 4,346,170).

L-lysine-producing or secreting strains of the Enterobacteriaceae family preferably have, inter alia, one or more of the genetic or phenotypical features selected from the group consisting of: resistance to lysine analogues, for example oxalysine, lysine hydroxamate, (S)-2-aminoethyl-L-cysteine (AEC), gamma-methyllysine, chlorocaprolactam and the like, desensitized aspartokinase, desensitized phosphoenolpyruvate carboxylase.

Examples which may be mentioned of a suitable parent strain which secretes or produces L-tryptophan, of the genus *Escherichia*, in particular the species *Escherichia coli* are:

*Escherichia coli* JP4735/pMU3028 (DSM10122) (U.S. Pat. No. 5,756,345)
*Escherichia coli* JP6015/pMU91 (05M10123) (U.S. Pat. No. 5,756,345)
*Escherichia coli* AGX17 (pGX44) (NRRL B-12263) (U.S. Pat. No. 4,371,614)

L-tryptophan-producing or secreting strains of the Enterobacteriaceae family preferably have, inter alia, one or more of the genetic or phenotypical features selected from the group consisting of: the activity of at least one enzyme selected from the group consisting of anthranilate synthase (trpE), phosphoglycerate dehydrogenase (serA), 3-deoxy-D-arabino-heptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB), may further be enhanced, the activity of chorismate mutase/prephenate dehydratase or chorismate mutase/prephenate dehydrogenase may further be attenuated, one or more of anthranilate synthase and phosphoglycerate dehydrogenase are released from the feedback inhibition by L-tryptophan and L-serine.

Examples which may be mentioned of a suitable parent strain which secretes or produces L-isoleucine, of the genus *Escherichia*, in particular the species *Escherichia coli* are:

*Escherichia coli* H-8670 (FERM BP-4051) (U.S. Pat. No. 5,460,958)
*Escherichia coli* H-8683 (FERM BP-4052) (U.S. Pat. No. 5,460,958)
*Escherichia coli* FERM BP-3628 (U.S. Pat. No. 5,362, 637)
*Escherichia coli* FERM BP-3629 (U.S. Pat. No. 5,362, 637)
*Escherichia coli* FERM BP-3630 (U.S. Pat. No. 5,362, 637)

*Escherichia coli* H-9146 (FERM BP-5055) (U.S. Pat. No. 5,695,972)

*Escherichia coli* H-9156 (FERM BP-5056) (U.S. Pat. No. 5,695,972).

L-isoleucine-producing or secreting strains of the Enterobacteriaceae family preferably have, inter alia, one or more of the genetic or phenotypical features selected from the group consisting of: resistance to isoleucine analogs such as thiaisoleucine, resistance to ethionine, resistance to arginine hydroxamate, resistance to S-(2-aminoethyl)-L-cysteine, resistance to D-serine.

An example which may be mentioned of a suitable parent strain which secretes or produces L-valine, of the genus *Escherichia*, in particular the species *Escherichia coli* is:

*Escherichia coli* AJ11502 (NRRL B-12288) (U.S. Pat. No. 4,391,907).

Examples which may be mentioned of a suitable parent strain which secretes or produces L-leucine, of the genus *Escherichia*, in particular the species *Escherichia coli* are:

*Escherichia coli* H-9070 (FERM BP-4704) (U.S. Pat. No. 5,744,331)

*Escherichia coli* H-9072 (FERM BP-4706) (U.S. Pat. No. 5,744,331).

L-leucine-producing or secreting strains of the Enterobacteriaceae family preferably have, inter alia, one or more of the genetic or phenotypical features selected from the group consisting of: resistance to leucine analogs such as 4-azaleucine or 5,5,5-trifluoroleucine, resistance to β-2-thienylalanine, where appropriate ability to utilize sucrose, enhancement of the leucine operon, increase in 2-isopropylmalate synthase, increase in 3-isopropylmalate dehydrogenase, increase in isopropylmalate isomerase, increase in leucine transaminase, increase in leucine aminotransferase, increase in the leucine exporter.

An example which may be mentioned of a suitable parent strain which secretes or produces L-alanine, of the genus *Escherichia*, in particular the species *Escherichia coli* is:

*Escherichia coli* strain K88 (FERM BP-4121) (U.S. Pat. No. 5,559,016)

Strains of the Enterobacteriaceae family which produce or secrete L-alanine preferably have, inter alia, a heterologous L-alanine dehydrogenase gene, preferably from the genera *Arthrobacter* or *Bacillus* or actinomycetes, particularly preferably from *Arthrobacter* sp. HAP1.

An example which may be mentioned of a suitable parent strain which secretes or produces L-histidine, of the genus *Escherichia*, in particular the species *Escherichia coli* is:

*Escherichia coli* AJ 11388 (FERM-P 5048, NRRL B-12121) (U.S. Pat. No. 4,388,405).

L-histidine-producing or secreting strains of the Enterobacteriaceae family preferably have, inter alia, one or more of the genetic or phenotypical features selected from the group consisting of: resistance to histidine analogs such as 2-thiazolalanine, 1,2,4-triazolalanine, 2-methyl histidine and histidine hydroxamate, where appropriate ability to utilize sucrose, enhancement of the histidine operon, increase in ATP phosphoribosyl transferase, increase in phosphoribosyl ATP pyrophosphohydrolase, increase in phosphoribosyl AMP cyclohydrolase, increase in cyclase HisF, increase in glutamine amidotransaminase HisH, increase in 1-(5-phosphoribosyl)-5-[(5-phosphoribosylamino)methylidene-amino]imidazole-4-carboxamide isomerase, increase in imidazole glycerol phosphate dehydratase, increase in histidinol phosphate transaminase, increase in histidinol phosphate phosphatase, increase in histidinol dehydrogenase.

In the studies on which the invention is based, microorganisms of the Enterobacteriaceae family which comprise a DNA fragment having promoter activity according to the present invention, which is functionally linked to a polynucleotide coding for a membrane protein or for a protein having the activity of an amino acid transporter such as an amino acid exporter like rhtC, were found to produce increasing amounts of L-amino acids, in particular L-threonine, L-homoserine, L-histidine, L-lysine, L-tryptophan, L-valine, L-leucine, and L-isoleucine and to concentrate them in the cell or in the medium.

The nucleotide sequences of the genes or open reading frames (ORF) of *Escherichia coli* are part of the prior art and can be found in the *Escherichia coli* genome sequence published by Blattner et al. (Science 277: 1453-1462 (1997)). Endogenous enzymes of the host (methionine aminopeptidase) are known to be able to remove the N-terminal amino acid methionine.

The nucleotide sequence of the polynucleotide coding for a protein having the activity of an amino acid exporter (rhtC gene) of *Salmonella enterica* and *Erwinia carotovora* which likewise belong to the Enterobacteriaceae family is also known (Accession No.: NC_003198 (REGION: complementary (3454404-3455024) and Accession No.: NC_004547 (REGION: complementary (4661556-4662179)). Further nucleotide sequences for the rhtC gene have been found in the following Enterobacteriaceae: *Shigella flexneri* (Accession No.: CP000266, AE005674, AE014073); *Shigella boydii* (Accession No.: CP000036); *Shigella dysenteriae* (Accession No.: CP000034); *Shigella sonnei* (Accession No.: CP000038); *Salmonella typhimurium* (Accession No.: AE008884); *Sodalis glossinidius* (Accession No.: AP008232).

The rhtC gene of *Escherichia coli* K12 is described inter alia by the following information:

Name: Amino acid exporter

Function: catalyzes L-threonine amino acid export by way of a threonine/proton antiporter function Reference: Zakataeva et al., FEBS Letters 452(3):228-32 (1999);

Kruse et al., Applied Microbiological Biotechnology 59(2-3):205-10 (2002)

Accession No.: NC000913 (Region: 4005780-4006400)

The encoded polypeptide is 206 amino acids in length.

Alternative gene name (from EcoCyc: Encyclopedia of *Escherichia coli* K-12 Genes and Metabolism, SRI International, Menlo Park, USA): b3823, yigJ The nucleic acid sequences can be found in the databases of the National Center for Biotechnology Information (NCBI) of the National Library of Medicine (Bethesda, Md., USA), the nucleotide sequence database of the European Molecular Biologies Laboratories (EMBL, Heidelberg, Germany and Cambridge, UK) or the DNA database of Japan (DDBJ, Mishima, Japan).

For reasons of clarity, the disclosed sequence of the rhtC gene of *Escherichia coli* is depicted under SEQ ID NO: 1. The protein encoded by this reading frame is depicted as SEQ ID NO: 2. The disclosed sequence of the rhtC gene of *Escherichia coli*, including the upstream and downstream nucleotide sequences, is depicted under SEQ ID NO: 10, and the protein encoded by this reading frame is depicted under SEQ ID NO: 11 (corresponds to SEQ ID NO: 2).

The genes or open reading frames described in the citations indicated may be used according to the invention. It is furthermore possible to use alleles of said genes or open reading frames, which are the result of the degeneracy of the genetic code or of functionally neutral sense mutations. Preference is given to using endogenous genes or endogenous open reading frames.

"Endogenous genes" or "endogenous nucleotide sequences" mean the genes present in the population of a species or open reading frames or alleles or nucleotide sequences.

Alleles of the rhtC gene which contain functionally neutral sense mutations include inter alia those which result in no more than 30 or no more than 20, preferably no more than 10 or no more than 5, very particularly preferably no more than 3 or no more than 2 or at least one, conservative amino acid substitution(s) in the protein encoded by them. The present invention refers to conservative amino acid substitutions as those in which amino acids are replaced by those having similar functionalities, charges, polarities or hydrophobicities.

In the case of the aromatic amino acids, the substitutions are said to be conservative when phenylalanine, tryptophan and tyrosine are substituted for each other. In the case of the hydrophobic amino acids, the substitutions are said to be conservative when leucine, isoleucine and valine are substituted for each other. In the case of the polar amino acids, the substitutions are said to be conservative when glutamine and asparagine are substituted for each other. In the case of the basic amino acids, the substitutions are said to be conservative when arginine, lysine and histidine are substituted for each other. In the case of the acid amino acids, the substitutions are said to be conservative when aspartic acid and glutamic acid are substituted for each other. In the case of the hydroxyl group-containing amino acids, the substitutions are said to be conservative when serine and threonine are substituted for each other.

In the same way, it is also possible to use nucleotide sequences which encode variants of said proteins, which variants additionally contain an extension or truncation by at least one (1) amino acid at the N terminus or C terminus. This extension or truncation amounts to not more than 40, 30, 20, 10, 5, 3 or 2 amino acids or amino acid residues.

The suitable alleles also include those which encode proteins in which at least one (1) amino acid has been inserted or deleted. The maximum number of such changes, termed indels, can affect 2, 3, 5, 10, but in no case more than 20, amino acids.

The suitable alleles furthermore include those which can be obtained by means of hybridization, in particular under stringent conditions, using SEQ ID NO: 1 or parts thereof or the sequences which are complementary thereto.

The skilled person finds instructions for identifying DNA sequences by means of hybridization in, inter alia, the manual "The DIG System Users Guide for Filter Hybridization" supplied by Boehringer Mannheim GmbH (Mannheim, Germany, 1993) and Liebl et al. (International Journal of Systematic Bacteriology 41: 255-260 (1991)). The hybridization takes place under stringent conditions, that is the only hybrids formed are those in which the probe and target sequence, i.e. the polynucleotides treated with the probe, are at least 70% identical. It is known that the stringency of the hybridization, including the washing steps, is influenced and/or determined by varying the buffer composition, the temperature and the salt concentration. In general, the hybridization reaction is carried out at a stringency which is relatively low as compared with that of the washing steps (Hybaid Hybridisation Guide, Hybaid Limited, Teddington, U K, 1996).

For example, a buffer corresponding to 5×SSC buffer can be used for the hybridization reaction at a temperature of approx. 50° C.-68° C. Under these conditions, probes can also hybridize with polynucleotides which possess less than 70% identity with the sequence of the probe. These hybrids are less stable and are removed by washing under stringent conditions. This can be achieved, for example, by lowering the salt concentration down to 2×SSC and, where appropriate, subsequently to 0.5×SSC (The DIG System User's Guide for Filter Hybridization, Boehringer Mannheim, Mannheim, Germany, 1995) with the temperature being adjusted to approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. Temperature ranges of approx. 64° C.-68° C. or approx. 66° C.-68° C. are preferred. It is possible, where appropriate, to lower the salt concentration down to a concentration corresponding to 0.2×SSC or 0.1×SSC. By means of increasing the hybridization temperature stepwise, in steps of approx. 1-2° C., from 50° C. to 68° C., it is possible to isolate polynucleotide fragments which, for example, possess at least 70%, or at least 80%, or at least 90%, at least 91%, at least 92%, at least 93%, at least 94%, at least 95%, at least 96%, at least 97%, at least 98%, or at least 99%, identity with the sequence of the probe employed or with the nucleotide sequences shown in SEQ ID NO: 1. Additional instructions for the hybridization can be obtained commercially in the form of what are termed kits (e.g. DIG Easy Hyb from Roche Diagnostics GmbH, Mannheim, Germany, Catalog No. 1603558).

Furthermore, when using strains of the Enterobacteriaceae family to produce L-amino acids, in particular L-threonine, L-homoserine, L-histidine, L-lysine, L-tryptophan, L-valine, L-leucine, and L-isoleucine, it may be advantageous, in addition to modulating the expression of genes coding for membrane proteins or for proteins having the activity of an amino acid transporter such as an amino acid exporter like rhtC, by any of the mutagenesis measures described above within the promoter region of said gene, to increase one or more enzymes of the known biosynthesis pathways or of amino acid transport or enzymes of anaplerotic metabolism or enzymes for producing reduced nicotinamide adenine dinucleotide phosphate or glycolysis enzymes or PTS enzymes or sulfur metabolism enzymes. The use of endogenous genes is generally preferred.

In this connection, the term "enhancement" describes increasing the intracellular activity or concentration of one or more enzymes or proteins encoded by the corresponding DNA in a microorganism by increasing, for example, the copy number of the gene or genes or of the ORF or ORFs by at least one (1) copy, functionally linking a strong promoter to said gene or using a gene or allele or ORF which encodes a corresponding enzyme or protein having a high activity, and, where appropriate, combining these measures.

It may be advantageous, where appropriate, to modulate also the expression or production level of one or more enzymes/proteins in a microorganism by e.g. only moderately increasing the intracellular concentration or activity of the respective enzyme/protein, since too high an increase in enzyme/protein concentration may result, for example, in defective cell division or altered cell morphology and even in toxicity (Guthrie and Wickner, Journal of Bacteriology 172(10):5555-5562 (1990); Genevaux P. et al.; EMBO Reports 5(2): 195-200 (2004)).

The term "moderately increase" describes increasing the intracellular activity or concentration of the corresponding protein by no more than 10 times, 8 times, 6 times, 4 times, 3 times, 2 times or 1.5 times, based on that of the wild-type protein or on the activity or concentration of the protein in the microorganism or parent strain which is non-recombinant for the corresponding enzyme or protein. A non-recombinant microorganism or parent strain means the microorganism which is subjected to enhancement or overexpression according to the invention.

To achieve an enhancement, it is possible to increase, for example, expression of the genes or open reading frames or alleles or the catalytical properties of the protein. The two measures may be combined, where appropriate.

To achieve overexpression, it is possible to increase, for example, the copy number of the corresponding genes or open reading frames or to mutate the promoter region and regulatory region or the ribosome binding site which is located upstream of the structural gene. Expression cassettes which are incorporated upstream of the structural gene act in the same way. It is also possible to increase expression during the course of the fermentative amino acid production through inducible promoters; in addition, using promoters for gene expression which permits a different chronological gene expression can also be advantageous. At the level of the translational regulation of gene expression, it is possible to increase the frequency of initiation (binding of the ribosome to the mRNA) or the rate of elongation (elongation phase). Expression is likewise improved by means of measures for extending the lifespan of the mRNA. Furthermore, the enzyme activity is also potentiated by preventing the enzyme protein from being broken down. The ORFs, genes or gene constructs can either be present in plasmids having different copy numbers or be integrated, and amplified, in the chromosome. Alternatively, overexpression of the genes concerned can also be achieved by altering the composition of the media and the conduct of the culture.

Methods for overexpression are adequately described in the prior art, for example in Makrides et al. (Microbiological Reviews 60 (3), 512-538 (1996)). Using vectors increases the copy number by at least one (1) copy. The vectors used can be plasmids as described, for example, in U.S. Pat. No. 5,538,873. The vectors used can also be phages, for example phage Mu, as described in EP 0332448, or phage lambda (λ). The copy number can also be increased by incorporating an additional copy into another site in the chromosome, for example into the att site of phage λ (Yu and Court, Gene 223, 77-81 (1998)).

Furthermore, replacing a start codon with the most common (77%) codon in *Escherichia coli*, ATG, can considerably improve translation because the AUG codon is two to three times more effective than, for example, the codons GUG and UUG (Khudyakov et al., FEBS Letters 232(2): 369-71 (1988); Reddy et al., Proceedings of the National Academy of Sciences of the USA 82(17):5656-60 (1985)). The sequences surrounding the start codon may also be optimized because combined effects of the start codon and the flanking regions have been described (Stenstrom et al., Gene 273(2):259-65 (2001); Hui et al., EMBO Journal 3(3):623-9 (1984)).

The skilled person can find general instructions in this regard in, inter alia, Chang and Cohen (Journal of Bacteriology 134: 1141-1156 (1978)), Hartley and Gregori (Gene 13: 347-353 (1981)), Amann and Brosius (Gene 40: 183-190 (1985)), de Broer et al. (Proceedings of the National Academy of Sciences of the United States of America 80: 21-25 (1983)), LaVallie et al. (BIO/TECHNOLOGY 11: 187-193 (1993)), in PCT/US97/13359, Llosa et al. (Plasmid 26: 222-224 (1991)), Quandt and Klipp (Gene 80: 161-169 (1989)), Hamilton et al. (Journal of Bacteriology 171: 4617-4622 (1989)), Jensen and Hammer (Biotechnology and Bioengineering 58: 191-195 (1998)) and known textbooks of genetics and molecular biology.

Plasmid vectors which can be replicated in Enterobacteriaceae, such as pACYC184-derived cloning vectors (Bartolomé et al.; Gene 102: 75-78 (1991)), pTrc99A (Amann et al.; Gene 69: 301-315 (1988)) or pSC101 derivatives (Vocke and Bastia; Proceedings of the National Academy of Sciences USA 80(21): 6557-6561 (1983)) can be used. In a process according to the invention, it is possible to use a strain, which is transformed with a plasmid vector which carries at least the rhtC gene, or nucleotide sequences, or alleles, which encode its gene product.

The term "transformation" is understood as meaning the uptake of an nucleic acid by a host (microorganism).

It is possible to use inter alia methods of directed mutagenesis described in the prior art for generating alleles used in the microorganisms employed for the process according to the invention.

Thus it is possible, for example for producing L-threonine, at the same time to enhance, in particular overexpress, one or more of the genes selected from the group consisting of at least one gene of the thrABC operon encoding aspartate kinase, homoserine dehydrogenase, homoserine kinase and threonine synthase (U.S. Pat. No. 4,278,765), the pyruvate carboxylase-encoding *Corynebacterium glutamicum* pyc gene (WO 99/18228), the phosphoenolpyruvate synthase-encoding pps gene (Molecular and General Genetics 231(2): 332-336 (1992); WO 97/08333), the phosphoenolpyruvate carboxylase-encoding ppc gene (WO 02/064808), the pntA and pntB genes encoding the subunits of pyridine transhydrogenase (European Journal of Biochemistry 158: 647-653 (1986); WO 95/11985), the threonine export carrier protein-encoding *Corynebacterium glutamicum* thrE gene (WO 01/92545), the glutamate dehydrogenase-encoding gdhA gene (Nucleic Acids Research 11: 5257-5266 (1983); Gene 23: 199-209 (1983); DE19907347), the ptsHIcrr operon ptsH gene encoding the phosphohistidine protein hexose phosphotransferase of the PTS phosphotransferase system (WO 03/004674), the ptsHIcrr operon ptsI gene encoding enzyme I of the PTS phosphotransferase system (WO 03/004674), the ptsHIcrr operon crr gene encoding the glucose-specific IIA component of the PTS phosphotransferase system (WO 03/004674), the ptsG gene encoding the glucose-specific IIBC component (WO 03/004670), the cysteine synthase A-encoding cysK gene (WO 03/006666), the cysB gene encoding the regulator of the cys regulon (WO 03/006666), the cysJIH operon cysJ gene encoding the NADPH sulfite reductase flavoprotein (WO 03/006666), the cysJIH operon cysI gene encoding the NADPH sulfite reductase hemoprotein (WO 03/006666), the adenylyl sulfate reductase-encoding cysJIH operon cysH gene (WO 03/006666), the sucABCD operon sucA gene encoding the decarboxylase subunit of 2-ketoglutarate dehydrogenase (WO 03/008614), the sucABCD operon sucB gene encoding the dihydrolipoyltranssuccinase E2 subunit of 2-ketoglutarate dehydrogenase (WO 03/008614), the sucABCD operon sucC gene encoding the β-subunit of succinyl-CoA synthetase (WO 03/008615), the sucABCD operon sucD gene encoding the α-subunit of succinyl-CoA synthetase (WO 03/008615), the gene product of the *Escherichia coli* open reading frame (ORF) yjcG (Accession Number NC000913 (region 4281276-4282925) of the National Center for Biotechnology Information (NCBI, Bethesda, Md., USA), the gene product of the *Escherichia coli* open reading frame (ORF) yibD (Accession Number NC000913 (region 3787070-3788104) of the National Center for Biotechnology Information (NCBI, Bethesda, Md., USA), the gene product of the *Escherichia coli* open reading frame (ORF) yaaU (Accession Number NC000913 (region 45807-47138) of the National Center for Biotechnology Information (NCBI, Bethesda, Md., USA), which reading frame is also referred to as yaaU-ORF, the rhtA gene encoding the L-threonine and L-homoserine exporter (Astaurova et al., Applied Biochemical Microbiology 21:611-616 (1985); RU Patent No. 974817), the rhtB gene encoding the L-homoserine and homoserine-lactone exporter (Zakataeva et al., FEBS Letters 452(3):228-232 (1999); EP 1013765131).

L-threonine-producing microorganisms of the Enterobacteriaceae family typically possess a feedback-resistant or desensitized aspartate kinase l/homoserine dehydrogenase I. Feedback-resistant aspartate kinase/homoserine dehydrogenase means aspartate kinase/homoserine dehydrogenase enzymes (encoded by thrA, EC:2.7.2.4/EC:1.1.1.3) which, in comparison with the wild form, are less sensitive to inhibition by threonine or mixtures of threonine and the threonine analog α-amino-β-hydroxyvaleric acid (AHV) or AHV alone. The genes or alleles encoding these desensitized enzymes are also referred to as thrA$^{FBR}$ alleles. The prior art describes thrA$^{FBR}$ alleles which encode aspartate kinase/homoserine dehydrogenase variants having amino acid substitutions in comparison with the wild-type protein. The coding region of the *Escherichia coli* thrA wild-type gene, corresponding to accession number 000096.2 of the NCBI database (Bethesda, Md., USA) is depicted in SEQ ID NO: 3 and the polypeptide encoded by this gene is depicted in SEQ ID NO: 4.

The nucleotide sequence of the *Serratia marcescens* thrA gene has also been disclosed and is available at the NCBI under the accession number X60821. The coding region of the *Serratia marcescens* thrA wild-type gene is depicted in SEQ ID NO: 5 and the polypeptide encoded by this gene is depicted in SEQ ID NO: 6.

The L-threonine-producing microorganisms of the Enterobacteriaceae family which have been employed for the measures of the invention preferably have a thrA allele which encodes an aspartate kinase/homoserine dehydrogenase variant having the amino acid sequence of SEQ ID NO: 4 or SEQ ID NO: 6, which sequence comprises one or more of the amino acid substitutions selected from the group consisting of:

ThrA E253K (replacement of L-glutamic acid in position 253 of the encoded aspartate kinase/homoserine dehydrogenase enzyme according to SEQ ID NO: 4 or SEQ ID NO: 6 with L-lysine; see Research Disclosure 505, 537 (2006)), ThrA G330D (replacement of glycine in position 330 of the encoded aspartate kinase/homoserine dehydrogenase enzyme according to SEQ ID NO: 4 or SEQ ID NO: 6 with L-aspartic acid; see Omori et al. (Journal of Bacteriology 175(3), 785-794 (1993)), ThrA S345F (replacement of L-serine in position 345 of the encoded aspartate kinase/homoserine dehydrogenase enzyme according to SEQ ID NO: 4 or SEQ ID NO: 6 with L-phenylalanine; see Lee et al., Journal of Bacteriology 185(18): 5442-5451 (2003)), ThrA S352, replacement of L-serine in position 352 of the encoded aspartate kinase/homoserine dehydrogenase enzyme according to SEQ ID NO: 4 or SEQ ID NO: 6 with L-phenylalanine, L-tyrosine, L-asparagine, L-alanine, L-arginine, L-glutamine, L-glutamic acid, L-histidine, L-leucine, L-methionine, L-tryptophan or L-valine, preferably with L-phenylalanine; see Omori et al. (Journal of Bacteriology 175(3), 785-794 (1993) and Omori et al. (Journal of Bacteriology 175(4), 959-965 (1993), ThrA A479T (replacement of L-alanine in position 479 of the encoded aspartate kinase/homoserine dehydrogenase enzyme according to SEQ ID NO: 4 or SEQ ID NO: 6 with L-threonine; see Omori et al. (Journal of Bacteriology 175(3), 785-794 (1993)).

Preference is given to either of the thrA$^{FBR}$ alleles, thrA E253K (replacement of L-glutamic acid in position 253 of the encoded aspartate kinase/homoserine dehydrogenase enzyme with L-lysine) or S345F (replacement of L-serine in position 345 of the encoded aspartate kinase/homoserine dehydrogenase enzyme with L-phenylalanine), according to SEQ ID NO: 4.

The thrA$^{FBR}$ alleles described herein which encode an aspartate kinase/homoserine dehydrogenase enzyme may be overexpressed using the above-described measures.

Furthermore, for the purpose of producing L-amino acids, in particular L-threonine, L-homoserine, L-histidine, L-lysine, L-tryptophan, L-valine, L-leucine, and L-isoleucine it may be advantageous, in addition to modulating the expression of genes coding for membrane proteins or for proteins having the activity of an amino acid transporter such as an amino acid exporter like rhtC, to eliminate undesired secondary reactions (Nakayama: "Breeding of Amino Acid Producing Microorganisms", in: Overproduction of Microbial Products, Krumphanzl, Sikyta, Vanek (eds.), Academic Press, London, U K, 1982).

Thus it is possible, for example, for the purpose of producing L-threonine, at the same time to attenuate, where appropriate eliminate or reduce expression of, one or more of the genes selected from the group consisting of the threonine dehydrogenase-encoding tdh gene (Journal of Bacteriology 169: 4716-4721 (1987)), the malate dehydrogenase (E.C. 1.1.1.37)-encoding mdh gene (Archives in Microbiology 149: 36-42 (1987)), the pckA gene encoding the enzyme phosphoenolpyruvate carboxykinase (WO 02/29080), the pyruvate oxidase-encoding poxB gene (WO 02/36797), the dgsA gene (WO 02/081721), which is also known under the name mlc gene, encoding the DgsA regulator of the phosphotransferase system, the fruR gene (WO 02/081698), which is also known under the name cra gene, encoding the fructose repressor, the rpoS gene (WO 01/05939), which is also known under the name katF gene, encoding the sigma$^{38}$ factor, and the aspartate ammonium lyase-encoding aspA gene (WO 03/008603).

These measures are carried out, where appropriate, in addition to or in a suitable combination with the specified measures of enhancing genes to increase threonine production.

In this context, the term "attenuation" describes the reduction or abolition, in a microorganism, of the intracellular activity or concentration of one or more enzymes or proteins which are encoded by the corresponding DNA, by, for example, using a weaker promoter than in the parent strain or microorganism not recombinant for the corresponding enzyme or protein, or a gene or allele which encodes a corresponding enzyme or protein having a low activity, or inactivating the corresponding enzyme or protein, or the open reading frame or gene, and, where appropriate, combining these measures.

In general, the attenuation measures lower the activity or concentration of the corresponding protein down to from 0 to 75%, from 0 to 50%, from 0 to 25%, from 0 to 10% or from 0 to 5% of the activity or concentration of the wild-type protein or of the activity or concentration of the protein for the parent strain or microorganism which is not recombinant for the corresponding enzyme or protein. The parent strain or microorganism which is not recombinant is understood as being the microorganism on which the attenuation or elimination according to the invention is is performed.

In order to achieve an attenuation, for example the expression of the genes or open reading frames, or the catalytic properties of the enzyme proteins, can be reduced or abolished. Where appropriate, both measures can be combined.

The gene expression can be reduced by carrying out the culture in a suitable manner, by genetically altering (mutating) the signal structures for the gene expression or also by means of the antisense RNA technique. Signal structures for the gene expression are, for example, repressor genes, activator genes, operators, promoters, attenuators, ribosome binding sites, the start codon and terminators. The skilled person can find information in this regard in, inter alia and for example, Jensen and Hammer (Biotechnology and Bioengineering 58: 191-195 (1998)), in Carrier and Keasling (Biotechnology Progress 15: 58-64 (1999)), in Franch and Gerdes (Current Opinion in Microbiology 3: 159-164 (2000)), Kawano et al. (Nucleic Acids Research 33(19), 6268-6276 (2005)) and in well known textbooks of genetics and molecular biology such as the textbook by Knippers ("Molekulare Genetik [Molecular Genetics]", 6th edition, Georg Thieme Verlag, Stuttgart, Germany, 1995) or that by Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art. Examples which may be mentioned are the articles by Qiu and Goodman (Journal of Biological Chemistry 272: 8611-8617 (1997)), Yano et al. (Proceedings of the National Academy of Sciences of the United States of America 95: 5511-5515 (1998)) and Wente and Schachmann (Journal of Biological Chemistry 266: 20833-20839 (1991)). Summaries can be found in known textbooks of genetics and molecular biology, such as that by Hagemann ("Allgemeine Genetik [General Genetics]", Gustav Fischer Verlag, Stuttgart, 1986).

Mutations which come into consideration are transitions, transversions, insertions and deletions of at least one (1) base pair or nucleotide. Depending on the effect of the mutation-elicited amino acid substitution on the enzyme activity, reference is made to missense mutations or to nonsense mutations. The missense mutation leads to a replacement of a given amino acid in a protein with a different amino acid, with the amino acid replacement in particular being non-conservative. This thereby impairs the functional ability or activity of the protein and reduces it down to a value of from 0 to 75%, 0 to 50%, 0 to 25%, 0 to 10% or 0 to 5%. The nonsense mutation leads to a stop codon in the coding region of the gene and thus to premature termination of the translation. Insertions or deletions of at least one base pair in a gene lead to frame shift mutations, which in turn result in incorrect amino acids being incorporated or in the translation being prematurely terminated. If a stop codon is formed in the coding region as a consequence of the mutation, this then also leads to translation being terminated prematurely. Deletions of at least one (1) or more codons typically also lead to complete loss of the enzyme activity. WO 03/074719 describes the reduction of gene expression by suppressing a stop codon mutation in the coding region, using suitable t-RNA suppressors.

Directions for generating these mutations belong to the prior art and can be obtained from known textbooks of genetics and molecular biology such as the textbook by Knippers ("Molekulare Genetik [Molecular Genetics]", 6th edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986).

Suitable mutations in the genes can be incorporated into suitable strains by means of gene or allele exchange.

A customary method is the method, described by Hamilton et al. (Journal of Bacteriology 171: 4617-4622 (1989)), of gene exchange using a conditionally replicating pSC101 derivative pMAK705. Other methods described in the prior art, such as that of Martinez-Morales et al. (Journal of Bacteriology 181: 7143-7148 (1999)) or that of Boyd et al. (Journal of Bacteriology 182: 842-847 (2000)), can also be used.

It is likewise possible to transfer mutations in the relevant genes, or mutations, which affect the expression of the relevant genes or open reading frames, into different strains by means of conjugation or transduction.

Where appropriate, any combination of the measures of enhancement and attenuation is possible.

The invention furthermore relates to a process for fermentatively preparing L-amino acids, in particular L-threonine, L-homoserine, L-histidine, L-lysine, L-tryptophan, L-valine, L-leucine, and L-isoleucine, using the aforementioned recombinant microorganisms of the Enterobacteriaceae family, in which additionally further enhanced, in particular overexpressed, genes of the biosynthesis pathway of the desired L-amino acid are present and/or in which the metabolic pathways that reduce the formation of the desired L-amino acid are at least partially attenuated.

The performance of the bacteria, or of the fermentation process using these bacteria, is improved, with regard to one or more of the parameters selected from the group consisting of the product concentration (product per volume), the product yield (product formed per carbon source consumed) and the product formation (product formed per volume and time), or else other process parameters and combinations thereof, by at least 0.5%, at least 1%, at least 1.5% or at least 2%, based on the non-recombinant microorganism or parent strain, or the fermentation process using this microorganism or parent strain.

According to the invention, the prepared microorganisms are cultured in a batch process, in a fed-batch process, in a repeated fed-batch process or in a continuous process (DE102004028859.3 or U.S. Pat. No. 5,763,230). Processes of this kind are summarized in the textbook by Chmiel (Bioprozesstechnik 1. Einführung in die Bioverfahrenstechnik [Bioprocess technology 1. Introduction to bioprocess technology](Gustav Fischer Verlag, Stuttgart, 1991)) or in the textbook by Storhas (Bioreaktoren and periphere Einrichtungen [Bioreactors and peripheral installations] (Vieweg Verlag, Braunschweig/Wiesbaden, 1994)).

In a batch process, all starting materials, apart from a few exceptions such as, for example, oxygen and pH correctants, are introduced in the form of a single reaction mixture, and the microorganism is cultured in the resulting medium.

In a fed-batch process, the microorganism is first cultured by means of a batch process (batch phase). This is followed by adding continually or batchwise a starting material, where appropriate also a plurality of starting materials, essential to preparing the product, to the culture (feed phase). In the case of preparing L-amino acids, said starting material is a carbon source.

A repeated fed-batch process is a fed-batch process in which, after fermentation has been completed, part of the fermentation broth obtained is used as inoculum for starting another repeated fed-batch process. This cycle may be repeated several times, where appropriate. Repeated fed-batch processes are described, for example, in WO 02/18543 and WO 05/014843.

In a continuous process, a batch or fed-batch process is followed by continually adding to the culture one or more, where appropriate all, starting materials and removing fermentation broth at the same time. Continuous processes are described, for example, in the patent documents U.S. Pat. No. 5,763,230, WO 05/014840, WO 05/014841 and WO 05/014842.

The culture medium to be used must satisfy the demands of the particular strains in a suitable manner. The American Society for Bacteriology Manual "Manual of Methods for General Bacteriology" (Washington D.C., USA, 1981) contains descriptions of media for culturing a variety of microorganisms. The terms culture medium, fermentation medium and nutrient medium and medium can be used interchangeably.

A culture medium usually contains inter alia one or more carbon source(s), nitrogen source(s) and phosphorus source(s).

Sugar and carbohydrates such as glucose, sucrose, lactose, fructose, maltose, molasses, starch and where appropriate cellulose, oils and fats, such as soybean oil, sunflower oil, peanut oil and coconut fat, fatty acids, such as palmitic acid, stearic acid and linoleic acid, alcohols, such as glycerol and ethanol, and organic acids, such as acetic acid, may be used as the carbon source. These substances may be used individually or as a mixture.

Organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate, may be used as the nitrogen source. The nitrogen sources may be used individually or as a mixture. Phosphoric acid, potassium dihydrogen phosphate or dipotassium hydrogen phosphate, or the corresponding sodium-containing salts, may be used as the phosphorus source.

In addition, the culture medium must contain salts of metals, such as magnesium sulfate or iron sulfate, which are required for growth. Finally, essential growth promoters, such as amino acids and vitamins, may be used in addition to the abovementioned substances. Suitable precursors can also be added to the culture medium. Said ingredients may be added to the culture in the form of a one-off mixture or suitably fed in during the culture.

The fermentation is generally carried out at a pH of from 5.5 to 9.0, in particular of from 6.0 to 8.0. Basic compounds, such as sodium hydroxide, potassium hydroxide, ammonia or ammonia water, or acidic compounds, such as phosphoric acid or sulfuric acid, are used in a suitable manner for controlling the pH of the culture. Antifoamants, such as fatty acid polyglycol esters, can be used for controlling foaming. Suitable selectively acting substances, for example antibiotics, can be added to the medium in order to maintain the stability of plasmids. Oxygen or oxygen-containing gas mixtures, such as air, are passed into the culture in order to maintain aerobic conditions. The temperature of the culture is normally from 25° C. to 45° C. and preferably from 30° C. to 40° C. The action of the microorganisms results in the L-amino acid being concentrated or accumulated in the fermentation or culture broth. The culture is continued until a maximum of the desired L-amino acid has been formed. This objective is normally reached within 10 to 160 hours. Longer culturing times are possible in continuous processes.

A fermentation broth or culture broth means a fermentation medium in which a microorganism has been cultured for a certain time and at a certain temperature.

After the fermentation has been completed, the fermentation broth obtained accordingly comprises a) the biomass (cell mass) of the microorganism, produced due to propagation of the cells of said microorganism, b) the L-amino acid produced in the course of the fermentation, c) the organic by-products produced in the course of the fermentation, and d) the components of the fermentation medium/fermentation media used and the starting materials such as, for example, vitamins such as thiamine or salts such as magnesium sulfate, which have not been consumed by said fermentation.

The culture broth or fermentation broth produced may subsequently be collected, and the desired L-amino acid or the L-amino acid-containing product may be recovered or isolated.

In one process variant, the fermentation broth is concentrated, where appropriate, and the L-amino acid is subsequently purified or isolated in a pure or virtually pure form. Ion exchange chromatography, crystallization, extraction processes and treatment with activated carbon are typical methods for purifying L-amino acids. These methods result in substantially pure L-amino acids, with a content of ≥90% by weight, ≥95% by weight, ≥96% by weight, ≥97% by weight, ≥98% by weight or ≥99% by weight.

It is likewise possible, in another process variant, to prepare a product from the fermentation broth produced by removing the biomass of the bacterium, which is present in the fermentation broth, completely (100%) or virtually completely, i.e. more than or greater than (>) 90%, >95%, >97%, >99%, and leaving the remaining constituents of the fermentation broth largely, i.e. to an extent of 30%-100%, 40%-100%, 50%-100%, 60%-100%, 70%-100%, 80%-100%, or 90%-100%, preferably greater than or equal to (≥) 50%, ≥60%, ≥70%, ≥80%, ≥90% or ≥95% or else completely (100%), in the product.

Separation methods such as centrifugation, filtration, decantation or flocculation, or a combination thereof, are used for removing or separating off the biomass.

The resulting broth is then inspissated or concentrated using known methods, for example using a rotary evaporator, a thin film evaporator or a falling film evaporator, by means of reverse osmosis or by means of nanofiltration, ora combination of these methods.

This concentrated broth is then worked-up into what is preferably a flowable, finely divided powder using the methods of freeze drying, spray drying or spray granulation, or using other methods. This flowable, finely divided powder can then in turn be converted into a coarse-grain, readily flowable, storable, and to a large extent dust-free, product using suitable compacting or granulating methods. A total of more than 90% of the water is removed in this connection, such that the water content in the product is less than 10% by weight, less than 5% by weight, less than 4% by weight or less than 3% by weight.

L-amino acids may be analyzed, in order to determine the concentration at one or more points in the course of the fermentation, by separating said L-amino acids by means of ion exchange chromatography, preferably cation exchange chromatography, followed by post-column derivatization using ninhydrin, as described in Spackman et al. (Analytical Chemistry 30: 1190-1206 (1958)). It is also possible to use ortho-phthadialdehyde rather than ninhydrin for post-column derivatization. An overview article on ion exchange chromatography can be found in Pickering (LC-GC (Magazine of Chromatographic Science) 7(6), 484-487 (1989)).

It is likewise possible to carry out a pre-column derivatization, for example by using ortho-phthadialdehyde or phenylisothiocyanate and to fractionate the amino acid derivatives obtained by reversed phase chromatography (RP), preferably in the form of high performance liquid chromatography (HPLC). Such a method is described, for example, in Lindroth et al. (Analytical Chemistry 51: 1167-1174 (1979)).

Detection is carried out photometrically (absorption, fluorescence).

A summary on amino acid analysis can be found, inter alia, in the textbook "Bioanalytik" [Bioanalytics] by Lottspeich and Zorbas (Spektrum Akademischer Verlag, Heidelberg, Germany 1998).

The process according to the invention is used for fermentatively preparing L-amino acids such as, for example, L-threonine, L-homoserine, L-histidine, L-lysine, L-tryptophan, L-valine, L-leucine, and L-isoleucine, in particular L-threonine.

BRIEF DESCRIPTION OF THE FIGURES

FIG. 1: Map of expression plasmid pMW219_P(allel) rhtC.

FIG. 2: Map of gene replacement vector pKO3rhtC-Pmut.

The base pair numbers stated are approximate values obtained in the context of reproducibility of measurements. The abbreviations and designations used have the following meaning:

BssHII: Cleavage site for the restriction enzyme BssHII
HindIII: Cleavage site for the restriction enzyme HindIII
KpnI: Cleavage site for the restriction enzyme KpnI
NcoI: Cleavage site for the restriction enzyme NcoI
SpeI: Cleavage site for the restriction enzyme SpeI
XbaI: Cleavage site for the restriction enzyme XbaI
Cm: Chloramphenicol resistance gene
Km: Kanamycin resistance gene
lacZ": 5' part of the lacZα gene fragment
'lacZ': 3' part of the lacZα gene fragment
oriC: Replication origin
rhtC: Gene for the threonine exporter protein RhtC
sacB: sacB gene
repA: Gene for the replication protein RepA Further details can be found in the examples.

In the following, the invention is illustrated by non-limiting examples and exemplifying embodiments.

EXAMPLES

The following microorganism was deposited at the German Collection of Microorganisms and Cell Cultures (DSMZ, Braunschweig, Germany) as a pure culture on 29 Apr. 1999, wherein deposition was converted into deposition in accordance with the Budapest Treaty on 31 Jul. 2000:

*Escherichia coli* strain DM1300 as DSM 12791.

The following microorganism was deposited at the German Collection of Microorganisms and Cell Cultures (DSMZ, Braunschweig, Germany) in accordance with the Budapest Treaty on 15 Jul. 2004:

*Escherichia coli* strain MG442 as DSM 16574.

The minimal media (M9) and complete media (LB) for *E. coli* are described by J. H. Miller (A short course in bacterial genetics (1992), Cold Spring Harbor Laboratory Press). Isolation of plasmid DNA from *E. coli* and all the techniques for restriction, Klenow treatment and alkaline phosphatase treatment were performed in accordance with Sambrook et al. (Molecular cloning. A laboratory manual (1989), Cold Spring Harbor Laboratory Press). The transformation of *E. coli*, unless stated otherwise, was performed in accordance with Chung et al. (Proceedings of the National Academy of Sciences of the United States of America, USA (1989) 86: 2172-2175). The incubation temperature when preparing strains and transformants is 37° C.

Example 1: Preparation of *Escherichia coli* K-12 Strain DM1180

DM1180 was prepared in several steps starting with strain VL334 which was purchased as CMIM B-1641 from the Russian National Collection of Industrial Microorganisms (VKPM, Moscow, Russia). The strain CMIM B-1641 is described in U.S. Pat. No. 4,278,765.

The incubation temperature during preparation of the strain was 37° C. In the case of the gene exchange process according to Hamilton et al., temperatures of 30° C. and 44° C. were used.

1. Transduction of the Scr Gene Locus

The bacteriophage P1 was multiplied in *E. coli* wild type strain H155 (Smith and Parsell, Journal of General Microbiology (1975) 87: 129-140) and *E. coli* K12 strain MG1655 (Guyer et al., Cold Spring Harbor Symp., Quant. Biology (1981) 45: 135-140) was infected with the isolated phage lysate. MG1655 transductants which could use sucrose as a source of carbon were obtained by plating onto sucrose-containing (2 g/l) minimal medium. A P1 lysate was again prepared from a selected clone, called MG1655scr+, and the strain VL334 was transduced with the phage lysate. The strain VL334scr+ was obtained after selection on sucrose-containing minimal medium.

2. Deletion of the Chromosomal Tdh Gene by Targeted Gene Exchange

To incorporate a deletion in the tdh gene, the method described by Hamilton et al. (Journal of Bacteriology (1989) 171: 4617-4622) was used, this being based on use of the plasmid pMAK705 with a temperature-sensitive replicon. The plasmid pDR121 (Ravnikar and Somerville, Journal of Bacteriology (1987) 169: 4716-4721) contains a 3.7 kilo base pair (kbp) large DNA fragment from *E. coli*, on which the tdh gene is encoded. To produce deletion of the tdh gene region, pDR121 was cleaved with restriction enzymes ClaI and EcoRV and the isolated 5 kbp large DNA fragment was ligated after treatment with the Klenow enzyme. The ligation mixture was transformed in *E. coli* strain DH5α and plasmid-containing cells were selected on LB agar to which 50 µg/ml of ampicillin had been added.

Successful deletion of the tdh gene could be demonstrated by plasmid DNA isolation and control cleavage with EcoRI. The 1.7 kbp large EcoRI fragment was isolated and ligated with the plasmid pMAK705, which had been partly digested with EcoRI. The ligation mixture was transformed in DH5α and plasmid-containing cells were selected on LB agar to which 20 µg/ml of chloramphenicol had been added. Successful cloning was demonstrated by plasmid DNA isolation and cleavage with EcoRI. The pMAK705 derivative produced was called pDM32.

For gene exchange, VL334scr+ was transformed with the plasmid pDM32. Exchange of the chromosomal tdh gene for the plasmid encoded deletion construct was performed using the selection process described by Hamilton et al. and was verified by standard PCR methods (Innis et al. (1990), PCR protocols. A guide to methods and Applications, Academic Press) using the following oligonucleotide primers:

```
Tdh1:
                                           (SEQ ID NO: 15)
5'-TCGCGACCTATAAGTTTGGG-3'

Tdh2:
                                           (SEQ ID NO: 16)
5'-AATACCAGCCCTTGTTCGTG-3'
```

This strain was called VL334scr+Δtdh.

3. Construction of the Plasmid pYN7parB

The plasmid pYN7 was isolated from the strain VL334/pYN7, which is deposited as CMIM B-1684 (U.S. Pat. No. 4,278,765) at the Russian National Collection of Industrial Microorganisms (VKPM, Moscow, Russia).

A 6.25 kbp long DNA fragment, which contained the thrABC-operon, was isolated from plasmid pYN7 with the aid of the restriction enzymes HindIII and BamHI by preparative agarose gel-electrophoresis.

The plasmid pBR322 (Bolivar et al., Gene 2, 95-113 (1977)) was purchased from Pharmacia Biotech Co. (Uppsala, Sweden) and treated with the restriction enzymes HindIII and BamHI. The 4.3 kbp long DNA fragment was isolated by preparative agarose gel electrophoresis. The two DNA fragments were mixed, treated with T4-DNA ligase and the strain DH5α was transformed with the ligation mixture. After selection on ampicillin-containing (50 µg/ml) LB agar transformants were obtained, which contained a plasmid, the structure of which corresponded to that of the plasmid pYN7.

The plasmid was isolated from a transformant, partly cleaved with the enzyme EcoRI and fully cleaved with the enzyme HindIII and ligated with the isolated parB gene region. For this, the plasmid pKG1022 (Gerdes, Biotechnology (1988) 6:1402-1405) was cleaved with the enzymes EcoRI and HindIII, the cleavage batch was separated out in 1% agarose gel and the 629 bp large parB fragment was isolated with the aid of the QIAquick Gel Extraction Kit (QIAGEN GmbH, Hilden, Germany). The ligation mixture was used to transform strain VL334scr+Δtdh. Selection of pYN7parB-containing cells was performed in LB agar to which had been added 50 µg/ml of ampicillin. Successful cloning of the parB gene region could be demonstrated by plasmid DNA isolation and control cleavage with EcoRI and HindIII.

4. Isolation of Threonine-Resistant Spontaneous Mutants

Starting with strain VL334scr+Δtdh/pYN7parB, spontaneous mutants were isolated on threonine-containing (60 g/l) minimal agar. Selected L-threonine-resistant individual colonies were further multiplied on minimal medium with the following composition: 3.5 g/l $Na_2HPO_4$*$2H_2O$, 1.5 g/l $KH_2PO_4$, 1 g/l $NH_4Cl$, 0.1 g/l $MgSO_4$*$7H_2O$, 2 g/l glucose, 20 g/l agar, 50 mg/l ampicillin.

A mutant called DM1180 was resistant to 60 g/l of L-threonine after this step, but in further experiments not stable in resistance and productivity. Moreover, no higher L-threonine resistance level could be achieved. DM1180 has many mutations that lead to resistance to α-amino-β-hydrovaleric acid, a mutation in the ilvA gene which causes an optionally partial and compensable L-isoleucine requirement, and a mutation in the tdh gene which causes threonine hydrogenase to be attenuated or switched off, and genes for using sucrose and has one resistance gene to ampicillin. The mutant strain DM1180 obtained was investigated by sequencing.

Example 2: Preparation of *Escherichia coli* K-12 Strain DM1300

In order to maintain stable strains in the further course of strain development, threonine resistance was decoupled from threonine synthesis by excluding the plasmid to strengthen threonine biosynthesis.

After incubation in antibiotic-free complete medium, plasmid-free derivatives were isolated from DM1180.

On appropriately supplemented minimal agar, those clones were then selected which exhibited an isoleucine and threonine auxotrophy and which were able to multiply on minimal medium which contained 60 g/l of L-threonine. One of these clones was transformed with the plasmid pYN7parB; selection of plasmid-containing cells was performed on ampicillin-containing complete medium. Then, isolation of the transformants took place on minimal medium with the following composition: 3.5 g/l $Na_2HPO_4$*$2H_2O$, 1.5 g/l $KH_2PO_4$, 1 g/l $NH_4Cl$, 0.1 g/l $MgSO_4$*$7H_2O$, 2 g/l glucose, 20 g/l agar, 50 mg/l ampicillin. Mutants with an increased threonine-resistance were then isolated on L-threonine-containing (80 g/l) minimal agar.

A mutant isolated in this way was called DM1300. This new strain is a L-methionine prototroph having resistance to at least 80 g/l of L-threonine.

Example 3: Threonine Production by Fed Batch Fermentation Using the Strains *Escherichia coli* *DM*1180 and DM1300

In order to compare capacity of the fermentative production of L-threonine an individual colony of the strains *Escherichia coli* DM1180 and DM1300 was multiplied on minimal agar with the following composition: 3.5 g/l $Na_2HPO_4$*$2H_2O$, 1.5 g/l $KH_2PO_4$, 1 g/l $NH_4Cl$, 0.1 g/l $MgSO_4$*$7H_2O$, 2 g/l sucrose, 20 g/l agar, 50 mg/l ampicillin. The culture was incubated for 5 days at 37° C. 10 ml of preliminary culture with the following composition: 2 g/l yeast extract, 10 g/l $(NH_4)_2SO_4$, 1 g/l $KH_2PO_4$, 0.5 g/l $MgSO_4$*$7H_2O$, 15 g/l $CaCO_3$, 20 g/l sucrose, 50 mg/l ampicillin, was inoculated with an inoculum and incubated for 16 hours at 37° C. and 180 rpm in an Infors HT Multitron standard incubator shaker from Infors AG (Bottmingen, Switzerland). A volume of 0.5 ml of this first liquid preliminary culture was transferred into 1402 g of preliminary culture medium M1-439 (Table 2). Batch fermentation was performed in 2 l stirred reactor fermenters from Sartorius (Sartorius Stedim Systems GmbH, Guxhagen, Germany, Model Biostat® B). Preliminary culture medium M1-439 contained the constituents listed in table 2. The culture was cultivated for 14.25 hours at a temperature of 37° C., with volume-specific aeration of 0.71 wm, an oxygen partial pressure of 10% of air saturation and a pH of 7.0.

A volume of 0.5 ml of this second liquid preliminary culture was transferred into 1402 g of preliminary culture medium A1-80 (Table 3). Batch fermentation was performed in 2 l stirred reactor fermenters from Sartorius (Sartorius Stedim Systems GmbH, Guxhagen, Germany, Model Biostat® B). Preliminary culture medium A1-80 contained the constituents listed in table 3. The culture was cultivated for 9.25 hours at a temperature of 37° C., with volume-specific aeration of 0.71 wm, an oxygen partial pressure of 10% of air saturation and a pH of 7.0.

In order to inoculate 1223 g of main culture medium M1-246 (Table 4), which was contained in 2 l stirred reactor fermenters from Sartorius (Sartorius Stedim Systems GmbH, Guxhagen, Germany, Model Biostat® B), 179 g of the third liquid preliminary culture in A1-80 medium were added. Main culture medium M1-246 contained the constituents listed in table 4. The culture was cultivated at a temperature of 37° C., with aeration of 1 l/min., a minimum stirrer speed of 800 rpm and a pH of 7.0 and an oxygen partial pressure of 10% of air saturation, until reaching a residual sugar concentration of 5 g/l. The culture was then cultivated for a further 30 hours at a temperature of 37° C., an oxygen partial pressure of 10% of air saturation and a pH of 7.0. During this time, 665 g of a sucrose solution with a concentration of 550.0 g/kg were added.

At different times, the optical density (OD) was determined with a photometer of the DR 2800 type from Hach Lange GmbH (Berlin, Germany) at a measured wavelength of 660 nm and the concentration of L-threonine formed was determined using a SYKAM S435 amino acid analyser from SYKAM Vertriebs GmbH (Fürstenfeldbruck, Germany) by ion-exchange chromatography and detection by post-column reaction with ninhydrin.

The results of this fermentations are given in table 1.

TABLE 1

| Strain | Threonine g/l | Cell density $OD_{660}$ | Yield % |
|---|---|---|---|
| DM1180 | 93.9 | 35.9 | 43.1 |
| DM1300 | 107.2 | 33.8 | 47.2 |

After 47.5 hours, an L-threonine concentration of 107.2 g/l was detected in the final sample from DM1300 fermentation in comparison to 93.9 g/l in the final sample from DM1180 fermentation.

TABLE 2

Composition of medium M1-439

| Component | Concentration (per kg) |
|---|---|
| Sucrose | 33.6 g |
| Yeast extract | 4.8 g |
| $(NH_4)_2SO_4$ | 4.8 g |
| $K_2HPO_4$ | 1.92 g |

TABLE 2-continued

Composition of medium M1-439

| Component | Concentration (per kg) |
|---|---|
| $MgSO_4 \cdot 7H_2O$ | 0.38 g |
| $FeSO_4 \cdot 7H_2O$ | 19 mg |
| $MnSO_4 \cdot H_2O$ | 12 mg |
| Ampicillin | 50 mg |
| Structol | 0.6 g |

TABLE 3

Composition of medium A1-80

| Component | Concentration (per kg) |
|---|---|
| Sucrose | 33.6 g |
| Yeast extract | 8.0 g |
| $(NH_4)_2SO_4$ | 4.8 g |
| $K_2HPO_4$ | 1.92 g |
| $MgSO_4 \cdot 7H_2O$ | 0.38 g |
| $FeSO_4 \cdot 7H_2O$ | 19 mg |
| $MnSO_4 \cdot H_2O$ | 12 mg |
| Structol | 0.6 g |

TABLE 4

Composition of medium M1-246

| Component | Concentration (per kg) |
|---|---|
| Sucrose | 33.6 g |
| Corn steep liquor | 10.0 g |
| $(NH_4)_2SO_4$ | 8.2 g |
| $K_2HPO_4$ | 1.00 g |
| $MgSO_4 \cdot 7H_2O$ | 0.38 g |
| $FeSO_4 \cdot 7H_2O$ | 20 mg |
| $MnSO_4 \cdot H_2O$ | 12 mg |
| Structol | 0.1 g |

Example 4: Sequencing

The mutant strain DM1300 obtained is investigated by sequencing and the genome sequence is compared to the sequence of DM1180

In this way a point mutation could be identified in the probable promoter area of the rhtC gene. The sequence of the wildtype promoter region of rhtC (PrhtC WT) is shown in SEQ ID NO: 7. The corresponding sequence of the mutated promoter region of rhtC (PrhtC allele) is shown in SEQ ID NO: 8.

Example 5: Constructing the Expression Plasmids pMW219_P(allel)rhtC and pMW219_P(WT)rhtC The E. coli K12 rhtC gene including the upstream region was amplified using the polymerase chain reaction (PCR) and synthetic oligonucleotides. PCR primers were synthesized (Eurofins Genomics GmbH, Ebersberg, Germany) on the basis of the nucleotide sequence of the rhtC gene in E. coli K-12 MG1655 (Accession Number NC_000913.3 (Region: 4007757-4008377), Blattner et al. (Science 277:1453-1474 (1997)):

PrhtC-1:

(SEQ ID NO: 17)

5'-GCATGTTGATGGCGATGACG-3'

PrhtC-2:

(SEQ ID NO: 18)

5'-CTGTTAGCATCGGCGAGGCA-3'.

The *E. coli* K-12 MG1655 and the *E. coli* DM1300 chromosomal DNA used for PCR was isolated using "QIAGEN DNeasy Blood & Tissue Kit" (QIAGEN GmbH, Hilden, Germany) in accordance with the manufacturers instructions. A DNA fragment of approx. 800 bp in size (SEQ ID NO: 12) was amplified under standard PCR conditions (Innis et al. (1990) PCR Protocols. A Guide to Methods and Applications, Academic Press) using Phusion DNA polymerase (New England Biolabs GmbH, Frankfurt, Germany) and the specific primers.

The amplified PrhtC fragments were cleaned up with QIAquick PCR Purification Kit (QIAGEN GmbH, Hilden, Germany) and each was then ligated to the low-copy vector pMW219 (Nippon Gene, Toyama, Japan) which has been digested with the enzyme SmaI. The *E. coli* strain DH5α (Grant et al.; Proceedings of the National Academy of Sciences USA 87:4645-4649 (1990)) was transformed with the ligation mixture and plasmid-harboring cells were selected on LB agar containing 50 µg of kanamycin/ml.

The fact that cloning has been successful can be demonstrated, after the plasmid DNA has been isolated, by performing a control cleavage using the enzymes KpnI/HindIII or BssHII. The plasmids are designated pMW219_P(allel) rhtC (FIG. 1) and pMW219_P(WT)rhtC.

Example 6: Preparing L-Threonine Using the Strains MG442/pMW219_P(allel)rhtC or pMW219_P(WT)rhtC The L-threonine-producing *E. coli* strain MG442 is described in the patent specification U.S. Pat. No. 4,278,765 and is deposited in the Russian national collection of industrial microorganisms (VKPM, Moscow, Russia) as CMIM B-1628 and at the German Collection of Microorganisms and Cell Cultures (DSMZ, Braunschweig, Germany) in accordance with the Budapest Treaty as DSM 16574. To test the effect of increasing the copy number of P(allel)rhtC and P(WT)rhtC the strain MG442 was transformed with the expression plasmids pMW219_P(allel)rhtC or pMW219_P(WT)rhtC described in example 5, and with the vector pMW219, and plasmid-harboring cells were selected on LB agar containing 50 µg of kanamycin/ml. This resulted in the strains MG442/pMW219_P(allel)rhtC, MG442/pMW219_P(WT)rhtC and MG442/pMW219. Selected individual colonies were then propagated further on minimal medium having the following composition: 3.5 g of Na$_2$HPO$_4$.2H$_2$O/l, 1.5 g of KH$_2$PO$_4$/l, 1 g of NH$_4$Cl/l, 0.1 g of MgSO$_4$.7H$_2$O/l, 2 g of glucose/l, 20 g of agar/l, 50 mg of kanamycin/l. The formation of L-threonine was checked in 10 ml batch cultures which were contained in 100 ml Erlenmeyer flasks. For this, a 10 ml preculture medium of the following composition: 2 g of yeast extract/l, 10 g of (NH$_4$)$_2$SO$_4$/l, 1 g of KH$_2$PO$_4$/l, 0.5 g of MgSO$_4$.7H$_2$O/l, 15 g of CaCO$_3$/l, 20 g of glucose/l, 50 mg of kanamycin/l, was inoculated and incubated, at 37° C. and 180 rpm for 16 hours, on an Infors HT Multitron standard incubator shaker from Infors AG (Bottmingen, Switzerland). In each case 250 µl of this preliminary culture were inoculated over into 10 ml of production medium (25 g of (NH$_4$)$_2$SO$_4$/l, 2 g of KH$_2$PO$_4$/l, 1 g of MgSO$_4$.7H$_2$O/l, 0.03 g of FeSO$_4$.7H$_2$O/l, 0.018 g of MnSO$_4$*1H$_2$O/l, 30 g of CaCO$_3$/l, 20 g of glucose/l, 50 mg of kanamycin/l) and incubated at 37° C. for 48 hours. After the incubation, the optical density (OD) of the culture suspension was determined at a measurement wavelength of 660 nm using the GENios™ plate reader from Tecan Group AG (Männedorf, Switzerland). A SYKAM S435 amino acid analyser from SYKAM Vertriebs GmbH (Fürstenfeldbruck, Germany) was then used to determine, by means of ion exchange chromatography and post-column reaction involving ninhydrin detection, the concentration of the resulting L-threonine in the culture supernatant, which has been sterilized by filtration. The results of the experiment are shown in table 5.

TABLE 5

| Strain | OD (660 nm) | L-Threonine g/l |
| --- | --- | --- |
| MG442/pMW219 | 5.1 | 1.8 |
| MG442/pMW219_P(WT)rhtC | 5.6 | 4.6 |
| MG442/pMW219_P(allel) rhtC | 4.9 | 5.9 |

In the L-threonine-low producer *E. coli* strain MG442, a significant increase in threonine production is seen through the plasmid-bound overexpression of rhtC, with the allele from DM1300 significantly more than with the WT rhtC.

The effect is more pronounced than described in EP 1 013 765, example 3. Here an accumulation of 10.2 g/L threonine with strain MG442/pVIC40, pRhtC is described whereas the control strain MG442/pVIC40 (with plasmid-bound increased expression of the thrABC genes) produces 4.9 g/L. The vector pRhtC is a pUC21 derivative that provides a high copy number of the rhtC gene in the bacterial cell, pMW219 derivatives are low copy plasmids. Obviously, a moderate expression level of rhtC is more beneficial for increasing the L-threonine productivity and the point mutation in the probable promoter area of the rhtC gene improves production capacities by further modulating the expression level in a favorable way.

Example 7: Preparing L-Threonine Using the Strains DM1300/pMW219_P(allel)rhtC or pMW219_P(WT)rhtC To test the effect of increasing the copy number of the two rhtC gene variants in a high producer strain able to synthesize more than 100 g/L L-threonine, *E. coli* strain DM1300, described in example 2, was transformed with the expression plasmids pMW219_P(allel)rhtC or pMW219_P(WT) rhtC described in example 5, and with the vector pMW219, and plasmid-harboring cells were selected on LB agar containing 50 µg of ampicillin/ml and 50 µg of kanamycin/ml. This resulted in the strains DM1300/pMW219_P(allel) rhtC, DM1300/pMW219_P(WT)rhtC and DM1300/pMW219. Selected individual colonies were then propagated further on minimal medium having the following composition: 3.5 g of Na$_2$HPO$_4$.2H$_2$O/l, 1.5 g of KH$_2$PO$_4$/l, 1 g of NH$_4$Cl/l, 0.1 g of MgSO$_4$.7H$_2$O/l, 2 g of sucrose/l, 20 g of agar/l, 50 µg of ampicillin/ml and 50 mg of kanamycin/l. The formation of L-threonine was checked in 10 ml batch cultures which were contained in 100 ml Erlenmeyer flasks. For this, a 10 ml preculture medium of the following composition: 2 g of yeast extract/l, 10 g of (NH$_4$)$_2$SO$_4$/l, 1 g of KH$_2$PO$_4$/l, 0.5 g of MgSO$_4$.7H$_2$O/l, 15 g of CaCO$_3$/l, 20 g of sucrose/l, 50 µg of ampicillin/ml and 50 mg of kanamycin/l, was inoculated and incubated, at 37° C. and 180 rpm for 16 hours, on an Infors HT Multitron standard incubator shaker from Infors AG (Bottmingen, Switzerland). In each case 250 µl of this preliminary culture were inoculated over into 10 ml of production medium (25 g of $(NH_4)_2SO_4/l$, 2 g of $KH_2PO_4/l$, 1 g of $MgSO_4.7H_2O/l$, 0.03 g of $FeSO_4.7H_2O/l$, 0.018 g of $MnSO_4*1H_2O/l$, 30 g of $CaCO_3/l$, 20 g of sucrose/l, 50 µg of ampicillin/ml and 50 mg of kanamycin/l) and incubated at 37° C. for 48 hours. After the incubation, the optical density (OD) of the culture suspension was determined at a measurement wavelength of 660 nm using the GENios™ plate reader from Tecan Group AG (Männedorf, Switzerland).

A SYKAM S435 amino acid analyser from SYKAM Vertriebs GmbH (Fürstenfeldbruck, Germany) was then used to determine, by means of ion exchange chromatography and post-column reaction involving ninhydrin detection, the concentration of the resulting L-threonine in the culture supernatant, which has been sterilized by filtration. The results of the experiment are shown in table 6.

TABLE 6

| Strain | OD (660 nm) | L-Threonine g/l |
|---|---|---|
| DM1180 | 4.9 | 8.9 |
| DM1300 | 5.2 | 12.6 |
| DM1300/pMW219 | 4.2 | 11.2 |
| DM1300/pMW219_P(WT)rhtC | 4.3 | 10.6 |
| DM1300/pMW219_P(allel)rhtC | 4.8 | 10.7 |

In general, the expression of a second plasmid decreases L-threonine production in the high producer strain because of the "metabolic burden" caused by the 2-plasmid system. But interestingly the same overexpression of P(WT)rhtC and P(allel)rhtC (low copy pMW219 derivative as in example 6 with basic producer strain MG442) leads to no improvement or even decrease of L-threonine production in comparison to the empty vector control DM1300/pMW219, the two alleles do not differ here.

To exclude any plasmid specific effects, we tested a different vector system by expressing the rhtC gene on pSU9parBrhtC, a multi copy derivative with the plasmid stabilizing region parB. This leads to a further reduction of L-threonine production in DM1300: Only 8.2 g/l L-threonine with an OD (660 nm) of 4.8 were produced with the same incubation conditions described above.

Obviously, too strong expression of rhtC is detrimental in a high producer strain.

Example 8: Construction of the Exchange Vector PKO3_P(allele)rhtC

The PrhtC allele was amplified using the polymerase chain reaction (PCR) and synthetic oligonucleotides. Based on the nucleotide sequence of the PrhtC gene in E. coli K12 MG1655 (accession number NC_000913.3, range: 4007757-4008377, Blatter et al. (Science 277:1453-1462 (1997)) PCR primers were synthesized (Eurofins Genomics GmbH, Ebersberg, Germany).

Primer Design and PCR reqQ_1
(SEQ ID NO: 19)
5' GCCGTTGTCTGGAAGAGAAG 3' rht1r
(SEQ ID NO: 20)
5' ATCAATCCACTTCGCCAGAC 3'

The chromosomal E. coli DM1300 DNA used for PCR was isolated according to manufacturers data with "QIAGEN DNeasy Blood & Tissue Kit" (QIAGEN GmbH, Hilden, Germany). With the two specific primers "regQ_1" and "rht1r" the fragment "P(allele)RhtC Insert" was amplified by PCR under standard PCR conditions (Innis et al.: PCR protocols. A guide to methods and applications, 1990, Academic Press) with the Phusion DNA polymerase (Thermo Fisher Scientific, Wattham, Mass. USA).

The resulting product "P(allele)RhtC_Insert" has a length of 1412 bp.

Cloning of the Insert into pKO3

The amplified "P(allele)RhtC_Insert" was ligated to the vector pCR-Blunt II-TOPO (Zero Blunt TOPO PCR Cloning Kit, Thermo Fisher Scientific, Wattham, Mass. USA) in accordance with the manufacturers instructions and transformed into the E. coli strain TOP10. Plasmid-harboring cells were selected on LB Agar containing 50 µg of kanamycin/ml. After the plasmid DNA has been isolated, the vector was cleaved with the enzyme NcoI and, after the cleavage has been checked in a 0.8% agarose gel, designated pCRBI-rhtC-Pmut.

The vector pCRBI-rhtC-Pmut was then cleaved with the enzymes XbaI and SpeI and the rhtC fragment was separated in a 0.8% agarose gel; it was then isolated from the gel (QIAguick Gel Extraction Kit, QIAGEN GmbH, Hilden, Germany) and ligated to the gene replacement vector pKO3 (Link et al, 1997, J. Bacteriol., 179, 20, 6228-6237).

The vector pKO3 was also cut with XbaI and at the same time dephosphorylated with alkaline Phosphatase. The digestion was purified by QIAguick PCR Purification Kit (QIAGEN GmbH, Hilden, Germany).

For ligation, vector and insert were ligated in the molar ratio of 1:3 with T4 ligase. Chemically competent cells of the E. coli strain NEB5alpha were transformed with 1 ml of the ligation mix and plated on LB agar with 20 mg/l Chloramphenicol. The plates were incubated 40 h at 30° C. Control of Plasmids Successful cloning is demonstrated by digesting the plasmid pKO3rhtC-Pmut with the restriction enzyme NcoI.

10 colonies were picked and cultivated overnight in 10 ml LB+20 mg/l Chloramphenicol at 30° C./180 rpm.

The next day 2 ml of the cultures were centrifuged and DNA preparations were made from the pellets. The ligation product can contain the insert in two orientations. Whether and in what orientation it is present can be checked with an NcoI-restriction digestion:

Insert in orientation A: fragments 1250 bp and 5912 BP
Insert in orientation B: fragments 930 BP and 6232 bp
pKO3 empty vector: Fragment 5681 bp (linearized)

The 10 plasmid clones were cut with NcoI and the products were separated on a 0.8% TAE agarose gel. A clone that contains the insert in orientation "A" was selected and referred to as "pKO3rhtC-Pmut".

The insert of this clone was sequenced with the primers "pKO3-L" and "PKO3-R".

PKO3-L
(SEQ ID NO: 21)
5' AGGGCAGGGTCGTTAAATAGC 3'

-continued

PKO3-R
(SEQ ID NO: 22)
5' TTAATGCGCCGCTACAGGGCG 3'

The DNA sequence of the amplified fragment "P(allele) RhtC_Insert" was determined using the primer "pKO3-L" and "PKO3-R" (Eurofins Genomics GmbH, Ebersberg, Germany). The expected sequence of the PrhtC allele has been confirmed and the cloned fragment is shown in SEQ ID NO: 14.

The created exchange vector pKO3rhtC-Pmut is shown in FIG. 2.

Example 9: Exchange of the rhtC Wild Type Promoter of MG442 Against the PrhtC Allele To introduce the PrhtC allele into the chromosome of *E. coli* L-threonine production strains the following method can be applied and is described exemplary with the location-specific mutagenesis of PrhtC in the *E. coli* strain MG442 (example 6).

For the exchange of the chromosomal rhtC promoter against the plasmid-encoded mutation construct, MG442 was transformed with the plasmid pKO3rhtC-Pmut. The gene exchange is performed using the selection procedure described by Link et al. (Journal of Bacteriology 179:6228-6237 (1997)) and has been verified by sequencing.

After the exchange, the PrhtC allele in MG442 shows the in SEQ ID NO: 7 represented form (sequencing by Eurofins Genomics GmbH, Ebersberg, Germany). The obtained strain is referred to as MG442_P(allele)RhtC.

Example 10: Preparing L-Threonine Using the Strain MG442_P(Allele)RhtC

Selected individual colonies of MG442_P(allele)RhtC and MG442 can be propagated on minimal medium having the following composition: 3.5 g of $Na_2HPO_4.2H_2O$/l, 1.5 g of $KH_2PO_4$/l, 1 g of $NH_4Cl$/l, 0.1 g of $MgSO_4.7H_2O$/l, 2 g of glucose/l, 20 g of agar/l. The formation of L-threonine can be checked in 10 ml batch cultures which are contained in 100 ml Erlenmeyer flasks. For this, a 10 ml preculture medium of the following composition: 2 g of yeast extract/l, 10 g of $(NH_4)_2SO_4$/l, 1 g of $KH_2PO_4$/l, 0.5 g of $MgSO_4.7H_2O$/l, 15 g of $CaCO_3$/l, 20 g of glucose/l, can be inoculated and incubated, at 37° C. and 180 rpm for 16 hours, on an Infors HT Multitron standard incubator shaker from Infors AG (Bottmingen, Switzerland). In each case 250 µl of this preliminary culture can be inoculated into 10 ml of production medium (25 g of $(NH_4)_2SO_4$/l, 2 g of $KH_2PO_4$/l, 1 g of $MgSO_4.7H_2O$/l, 0.03 g of $FeSO_4.7H_2O$/l, 0.018 g of $MnSO_4*1H_2O$/l, 30 g of $CaCO_3$/l, 20 g of glucose/l) and incubated at 37° C. for 48 hours. After the incubation, the optical density (OD) of the culture suspension can be determined at a measurement wavelength of 660 nm using the GENios™ plate reader from Tecan Group AG (Männedorf, Switzerland).

A SYKAM S435 amino acid analyser from SYKAM Vertriebs GmbH (Fürstenfeldbruck, Germany) then can be used to determine, by means of ion exchange chromatography and post-column reaction involving ninhydrin detection, the concentration of the resulting L-threonine in the culture supernatant, which has been sterilized by filtration.

All references cited herein are fully incorporated by reference. Having now fully described the invention, it will be understood by those of skilled in the art that the invention may be practiced within a wide and equivalent range of conditions, parameters and the like, without affecting the spirit or scope of the invention or any embodiment thereof.

The following sequences are contained in the sequence protocol:

| SEQ ID No.: | Description: |
|---|---|
| 1 | Nucleotide sequence of the *Escherichia coli* rhtC gene |
| 2 | Amino acid sequence of the *Escherichia coli* RhtC protein |
| 3 | Nucleotide sequence of the *Escherichia coli* thrA gene |
| 4 | Amino acid sequence of the *Escherichia coli* ThrA protein |
| 5 | Nucleotide sequence of the *Serratia marcescens* thrA gene |
| 6 | Amino acid sequence of the *Serratia marcescens* ThrA protein |
| 7 | Nucleotide sequence of the wild type *Escherichia coli* rhtC promoter |
| 8 | Nucleotide sequence of the mutated *Escherichia coli* rhtC promoter |
| 9 | Nucleotide sequence of the wild type *Escherichia coli* rhtC promoter with naturally occurring 5'-flanking region |
| 10 | Nucleotide sequence of the rhtC gene of *Escherichia coli*, including the upstream and downstream nucleotide sequences |
| 11 | Amino acid sequence of the *Escherichia coli* RhtC protein |
| 12 | Nucleotide sequence of the DNA sequence 0.8 kbp long containing the rhtC gene (here with mutation) |
| 13 | Amino acid sequence of the RhtC protein |
| 14 | Nucleotide sequence of the DNA sequence 1.4 kbp long containing the allelic rhtC exchange fragment |
| 15 | Nucleotide sequence of the primer Tdh1 |
| 16 | Nucleotide sequence of the primer Tdh2 |
| 17 | Nucleotide sequence of the primer PrhtC-1 |
| 18 | Nucleotide sequence of the primer PrhtC-2 |
| 19 | Nucleotide sequence of the primer reqQ_1 |
| 20 | Nucleotide sequence of the primer rht1r |
| 21 | Nucleotide sequence of the primer PKO3-L |
| 22 | Nucleotide sequence of the primer PKO3-R |

What is claimed is:

1. A recombinant L-amino acid-secreting microorganism of the Enterobacteriaceae family, comprising an DNA fragment having promoter activity that is functionally linked to a polynucleotide coding for a membrane protein, wherein the DNA fragment having promoter activity comprises the sequence of SEQ ID NO: 8.

2. The microorganism of claim 1, wherein the DNA fragment having promoter activity is linked at the 3' end to a second DNA fragment carrying a ribosome-binding site.

3. The microorganism of claim 1, wherein the DNA fragment having promoter activity is linked at the 3' end to a second DNA fragment comprising the nucleotide sequence of positions 174 to 204 of SEQ ID NO: 9.

4. The microorganism of claim 1, wherein the DNA fragment having promoter activity is linked at the 3' end to a second DNA fragment having the nucleotide sequence of positions 174 to 204 of SEQ ID NO: 9 which is linked at its 3' end to a polynucleotide coding for the membrane protein.

5. The microorganism of claim 1, wherein the DNA fragment having promoter activity is linked at the 5' end to a DNA fragment having the nucleotide sequence of positions 1 to 138 of SEQ ID NO: 9.

6. The microorganism of claim 1, wherein the membrane protein has the activity of an amino acid transporter.

7. The microorganism of claim 6, wherein the protein having the activity of an amino acid transporter is a protein having the activity of an amino acid exporter.

8. The microorganism of claim 7, wherein the protein having the activity of an amino acid exporter has an amino acid sequence which is at least 90% identical to the sequence of SEQ ID NO: 2.

9. The microorganism of claim 8, wherein the protein having the activity of an amino acid exporter has an amino acid sequence, which is at least 95% identical to the sequence of SEQ ID NO: 2.

10. The microorganism of claim 9, wherein the protein having the activity of an amino acid exporter comprises the amino acid sequence of SEQ ID NO: 2, and/or is encoded by a polynucleotide comprising the nucleotide sequence of SEQ ID NO: 1.

11. The microorganism of claim 1, wherein the DNA fragment having promoter activity is present in the chromosome of the microorganism, or, alternatively, the DNA fragment having promoter activity is located on an extrachromosomal replicating vector.

12. The microorganism of claim 1, wherein said microorganism produces L-threonine, L-homoserine, L histidine, L-lysine, L-tryptophan, L valine, L-leucine, and L-isoleucine.

13. The microorganism of claim 4, wherein the DNA fragment having promoter activity is linked at the 5' end to a DNA fragment having the nucleotide sequence of positions 1 to 138 of SEQ ID NO: 9.

14. The microorganism of claim 13, wherein the membrane protein has the activity of an amino acid exporter and comprises the amino acid sequence of SEQ ID NO: 2, and/or is encoded by a polynucleotide comprising the nucleotide sequence of SEQ ID NO: 1.

15. A process for preparing L amino acids or feedstuff additives containing L-amino acids, the process comprising:
  (i) fermenting the microorganism of claim 1 in a medium;
  (ii) enriching the L-amino acid in the fermentation medium and/or in the cell; and optionally
  (iii) isolating the L-amino acid.

16. A DNA fragment having promoter activity that is functionally linked to a polynucleotide coding for a membrane protein, wherein the DNA fragment having promoter activity comprises SEQ ID NO: 8.

* * * * *

SEQUENCE LISTING

```
<160> NUMBER OF SEQ ID NOS: 22

<210> SEQ ID NO 1
<211> LENGTH: 621
<212> TYPE: DNA
<213> ORGANISM: Escherichia coli
<220> FEATURE:
<221> NAME/KEY: CDS
<222> LOCATION: (1)..(621)
<223> OTHER INFORMATION: rhtC coding region

<400> SEQUENCE: 1 atg ttg atg tta ttt ctc acc gtc gcc atg gtg cac att gtg gcg ctt      48
Met Leu Met Leu Phe Leu Thr Val Ala Met Val His Ile Val Ala Leu
```

```
   1               5                  10                 15
atg agc ccc ggt ccc gat ttc ttt ttt gtc tct cag acc gct gtc agt    96
Met Ser Pro Gly Pro Asp Phe Phe Phe Val Ser Gln Thr Ala Val Ser
         20                  25                  30 cgt tcc cgt aaa gaa gcg atg atg ggc gtg ctg ggc att acc tgc ggc   144
Arg Ser Arg Lys Glu Ala Met Met Gly Val Leu Gly Ile Thr Cys Gly
             35                  40                  45 gta atg gtt tgg gct ggg att gcg ctg ctt ggc ctg cat ttg att atc   192
Val Met Val Trp Ala Gly Ile Ala Leu Leu Gly Leu His Leu Ile Ile
 50                  55                  60 gaa aaa atg gcc tgg ctg cat acg ctg att atg gtg ggc ggt ggc ctg   240
Glu Lys Met Ala Trp Leu His Thr Leu Ile Met Val Gly Gly Gly Leu
 65                  70                  75                  80 tat ctc tgc tgg atg ggt tac cag atg cta cgt ggt gca ctg aaa aaa   288
Tyr Leu Cys Trp Met Gly Tyr Gln Met Leu Arg Gly Ala Leu Lys Lys
                 85                  90                  95 gag gcg gtt tct gca cct gcg cca cag gtc gag ctg gcg aaa agt ggg   336
Glu Ala Val Ser Ala Pro Ala Pro Gln Val Glu Leu Ala Lys Ser Gly
            100                 105                 110 cgc agt ttc ctg aaa ggt tta ctg acc aat ctc gct aat ccg aaa gcg   384
Arg Ser Phe Leu Lys Gly Leu Leu Thr Asn Leu Ala Asn Pro Lys Ala
        115                 120                 125 att atc tac ttt ggc tcg gtg ttc tca ttg ttt gtc ggt gat aac gtt   432
Ile Ile Tyr Phe Gly Ser Val Phe Ser Leu Phe Val Gly Asp Asn Val
    130                 135                 140 ggc act acc gcg cgc tgg ggc att ttt gcg ctg atc att gtc gaa acg   480
Gly Thr Thr Ala Arg Trp Gly Ile Phe Ala Leu Ile Ile Val Glu Thr
145                 150                 155                 160 ctg gcg tgg ttt acc gtc gtt gcc agc ctg ttt gcc ctg ccg caa atg   528
Leu Ala Trp Phe Thr Val Val Ala Ser Leu Phe Ala Leu Pro Gln Met
                165                 170                 175 cgc cgt ggt tat caa cgt ctg gcg aag tgg att gat ggt ttt gcc ggg   576
Arg Arg Gly Tyr Gln Arg Leu Ala Lys Trp Ile Asp Gly Phe Ala Gly
            180                 185                 190 gcg tta ttt gcc gga ttt ggc att cat ttg att att tcg cgg tga       621
Ala Leu Phe Ala Gly Phe Gly Ile His Leu Ile Ile Ser Arg
        195                 200                 205
```

<210> SEQ ID NO 2
<211> LENGTH: 206
<212> TYPE: PRT
<213> ORGANISM: Escherichia coli

<400> SEQUENCE: 2

```
Met Leu Met Leu Phe Leu Thr Val Ala Met Val His Ile Val Ala Leu
  1               5                  10                  15

Met Ser Pro Gly Pro Asp Phe Phe Phe Val Ser Gln Thr Ala Val Ser
             20                  25                  30

Arg Ser Arg Lys Glu Ala Met Met Gly Val Leu Gly Ile Thr Cys Gly
         35                  40                  45

Val Met Val Trp Ala Gly Ile Ala Leu Leu Gly Leu His Leu Ile Ile
 50                  55                  60

Glu Lys Met Ala Trp Leu His Thr Leu Ile Met Val Gly Gly Gly Leu
 65                  70                  75                  80

Tyr Leu Cys Trp Met Gly Tyr Gln Met Leu Arg Gly Ala Leu Lys Lys
                 85                  90                  95

Glu Ala Val Ser Ala Pro Ala Pro Gln Val Glu Leu Ala Lys Ser Gly
            100                 105                 110
```

```
Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
            195                 200                 205

<210> SEQ ID NO 3
<211> LENGTH: 2463
<212> TYPE: DNA
<213> ORGANISM: Escherichia coli
<220> FEATURE:
<221> NAME/KEY: CDS
<222> LOCATION: (1)..(2463)
<223> OTHER INFORMATION: thrA coding region

<400> SEQUENCE: 3
```

| | | | | | | | | | | | | | | | | |
|---|---|---|---|---|---|---|---|---|---|---|---|---|---|---|---|---|
| atg | cga | gtg | ttg | aag | ttc | ggc | ggt | aca | tca | gtg | gca | aat | gca | gaa | cgt | 48 |
| Met | Arg | Val | Leu | Lys | Phe | Gly | Gly | Thr | Ser | Val | Ala | Asn | Ala | Glu | Arg | |
| 1 | | | | 5 | | | | | 10 | | | | | 15 | | |
| ttt | ctg | cgt | gtt | gcc | gat | att | ctg | gaa | agc | aat | gcc | agg | cag | ggg | cag | 96 |
| Phe | Leu | Arg | Val | Ala | Asp | Ile | Leu | Glu | Ser | Asn | Ala | Arg | Gln | Gly | Gln | |
| | | | 20 | | | | | 25 | | | | | 30 | | | |
| gtg | gcc | acc | gtc | ctc | tct | gcc | ccc | gcc | aaa | atc | acc | aac | cac | ctg | gtg | 144 |
| Val | Ala | Thr | Val | Leu | Ser | Ala | Pro | Ala | Lys | Ile | Thr | Asn | His | Leu | Val | |
| | | 35 | | | | | 40 | | | | | 45 | | | | |
| gcg | atg | att | gaa | aaa | acc | att | agc | ggc | cag | gat | gct | tta | ccc | aat | atc | 192 |
| Ala | Met | Ile | Glu | Lys | Thr | Ile | Ser | Gly | Gln | Asp | Ala | Leu | Pro | Asn | Ile | |
| | 50 | | | | | 55 | | | | | 60 | | | | | |
| agc | gat | gcc | gaa | cgt | att | ttt | gcc | gaa | ctt | ttg | acg | gga | ctc | gcc | gcc | 240 |
| Ser | Asp | Ala | Glu | Arg | Ile | Phe | Ala | Glu | Leu | Leu | Thr | Gly | Leu | Ala | Ala | |
| 65 | | | | | 70 | | | | | 75 | | | | | 80 | |
| gcc | cag | ccg | ggg | ttc | ccg | ctg | gcg | caa | ttg | aaa | act | ttc | gtc | gat | cag | 288 |
| Ala | Gln | Pro | Gly | Phe | Pro | Leu | Ala | Gln | Leu | Lys | Thr | Phe | Val | Asp | Gln | |
| | | | | 85 | | | | | 90 | | | | | 95 | | |
| gaa | ttt | gcc | caa | ata | aaa | cat | gtc | ctg | cat | ggc | att | agt | ttg | ttg | ggg | 336 |
| Glu | Phe | Ala | Gln | Ile | Lys | His | Val | Leu | His | Gly | Ile | Ser | Leu | Leu | Gly | |
| | | | 100 | | | | | 105 | | | | | 110 | | | |
| cag | tgc | ccg | gat | agc | atc | aac | gct | gcg | ctg | att | tgc | cgt | ggc | gag | aaa | 384 |
| Gln | Cys | Pro | Asp | Ser | Ile | Asn | Ala | Ala | Leu | Ile | Cys | Arg | Gly | Glu | Lys | |
| | | 115 | | | | | 120 | | | | | 125 | | | | |
| atg | tcg | atc | gcc | att | atg | gcc | ggc | gta | tta | gaa | gcg | cgc | ggt | cac | aac | 432 |
| Met | Ser | Ile | Ala | Ile | Met | Ala | Gly | Val | Leu | Glu | Ala | Arg | Gly | His | Asn | |
| | 130 | | | | | 135 | | | | | 140 | | | | | |
| gtt | act | gtt | atc | gat | ccg | gtc | gaa | aaa | ctg | ctg | gca | gtg | ggg | cat | tac | 480 |
| Val | Thr | Val | Ile | Asp | Pro | Val | Glu | Lys | Leu | Leu | Ala | Val | Gly | His | Tyr | |
| 145 | | | | | 150 | | | | | 155 | | | | | 160 | |
| ctc | gaa | tct | acc | gtc | gat | att | gct | gag | tcc | acc | cgc | cgt | att | gcg | gca | 528 |
| Leu | Glu | Ser | Thr | Val | Asp | Ile | Ala | Glu | Ser | Thr | Arg | Arg | Ile | Ala | Ala | |
| | | | | 165 | | | | | 170 | | | | | 175 | | |
| agc | cgc | att | ccg | gct | gat | cac | atg | gtg | ctg | atg | gca | ggt | ttc | acc | gcc | 576 |
| Ser | Arg | Ile | Pro | Ala | Asp | His | Met | Val | Leu | Met | Ala | Gly | Phe | Thr | Ala | |
| | | | 180 | | | | | 185 | | | | | 190 | | | |
| ggt | aat | gaa | aaa | ggc | gaa | ctg | gtg | gtg | ctt | gga | cgc | aac | ggt | tcc | gac | 624 |

```
Gly Asn Glu Lys Gly Glu Leu Val Val Leu Gly Arg Asn Gly Ser Asp
            195                 200                 205 tac tct gct gcg gtg ctg gct gcc tgt tta cgc gcc gat tgt tgc gag        672
Tyr Ser Ala Ala Val Leu Ala Ala Cys Leu Arg Ala Asp Cys Cys Glu
210                 215                 220 att tgg acg gac gtt gac ggg gtc tat acc tgc gac ccg cgt cag gtg        720
Ile Trp Thr Asp Val Asp Gly Val Tyr Thr Cys Asp Pro Arg Gln Val
225                 230                 235                 240 ccc gat gcg agg ttg ttg aag tcg atg tcc tac cag gaa gcg atg gag        768
Pro Asp Ala Arg Leu Leu Lys Ser Met Ser Tyr Gln Glu Ala Met Glu
            245                 250                 255 ctt tcc tac ttc ggc gct aaa gtt ctt cac ccc cgc acc att acc ccc        816
Leu Ser Tyr Phe Gly Ala Lys Val Leu His Pro Arg Thr Ile Thr Pro
        260                 265                 270 atc gcc cag ttc cag atc cct tgc ctg att aaa aat acc gga aat cct        864
Ile Ala Gln Phe Gln Ile Pro Cys Leu Ile Lys Asn Thr Gly Asn Pro
    275                 280                 285 caa gca cca ggt acg ctc att ggt gcc agc cgt gat gaa gac gaa tta        912
Gln Ala Pro Gly Thr Leu Ile Gly Ala Ser Arg Asp Glu Asp Glu Leu
290                 295                 300 ccg gtc aag ggc att tcc aat ctg aat aac atg gca atg ttc agc gtt        960
Pro Val Lys Gly Ile Ser Asn Leu Asn Asn Met Ala Met Phe Ser Val
305                 310                 315                 320 tct ggt ccg ggg atg aaa ggg atg gtc ggc atg gcg gcg cgc gtc ttt       1008
Ser Gly Pro Gly Met Lys Gly Met Val Gly Met Ala Ala Arg Val Phe
            325                 330                 335 gca gcg atg tca cgc gcc cgt att tcc gtg gtg ctg att acg caa tca       1056
Ala Ala Met Ser Arg Ala Arg Ile Ser Val Val Leu Ile Thr Gln Ser
        340                 345                 350 tct tcc gaa tac agc atc agt ttc tgc gtt cca caa agc gac tgt gtg       1104
Ser Ser Glu Tyr Ser Ile Ser Phe Cys Val Pro Gln Ser Asp Cys Val
    355                 360                 365 cga gct gaa cgg gca atg cag gaa gag ttc tac ctg gaa ctg aaa gaa       1152
Arg Ala Glu Arg Ala Met Gln Glu Glu Phe Tyr Leu Glu Leu Lys Glu
370                 375                 380 ggc tta ctg gag ccg ctg gca gtg acg gaa cgg ctg gcc att atc tcg       1200
Gly Leu Leu Glu Pro Leu Ala Val Thr Glu Arg Leu Ala Ile Ile Ser
385                 390                 395                 400 gtg gta ggt gat ggt atg cgc acc ttg cgt ggg atc tcg gcg aaa ttc       1248
Val Val Gly Asp Gly Met Arg Thr Leu Arg Gly Ile Ser Ala Lys Phe
            405                 410                 415 ttt gcc gca ctg gcc cgc gcc aat atc aac att gtc gcc att gct cag       1296
Phe Ala Ala Leu Ala Arg Ala Asn Ile Asn Ile Val Ala Ile Ala Gln
        420                 425                 430 gga tct tct gaa cgc tca atc tct gtc gtg gta aat aac gat gat gcg       1344
Gly Ser Ser Glu Arg Ser Ile Ser Val Val Val Asn Asn Asp Asp Ala
    435                 440                 445 acc act ggc gtg cgc gtt act cat cag atg ctg ttc aat acc gat cag       1392
Thr Thr Gly Val Arg Val Thr His Gln Met Leu Phe Asn Thr Asp Gln
450                 455                 460 gtt atc gaa gtg ttt gtg att ggc gtc ggt ggc gtt ggc ggt gcg ctg       1440
Val Ile Glu Val Phe Val Ile Gly Val Gly Gly Val Gly Gly Ala Leu
465                 470                 475                 480 ctg gag caa ctg aag cgt cag caa agc tgg ctg aag aat aaa cat atc       1488
Leu Glu Gln Leu Lys Arg Gln Gln Ser Trp Leu Lys Asn Lys His Ile
            485                 490                 495 gac tta cgt gtc tgc ggt gtt gcc aac tcg aag gct ctg ctc acc aat       1536
Asp Leu Arg Val Cys Gly Val Ala Asn Ser Lys Ala Leu Leu Thr Asn
        500                 505                 510
```

```
                                                       -continued
gta cat ggc ctt aat ctg gaa aac tgg cag gaa gaa ctg gcg caa gcc    1584
Val His Gly Leu Asn Leu Glu Asn Trp Gln Glu Glu Leu Ala Gln Ala
        515                 520                 525 aaa gag ccg ttt aat ctc ggg cgc tta att cgc ctc gtg aaa gaa tat    1632
Lys Glu Pro Phe Asn Leu Gly Arg Leu Ile Arg Leu Val Lys Glu Tyr
530                 535                 540 cat ctg ctg aac ccg gtc att gtt gac tgc act tcc agc cag gca gtg    1680
His Leu Leu Asn Pro Val Ile Val Asp Cys Thr Ser Ser Gln Ala Val
545                 550                 555                 560 gcg gat caa tat gcc gac ttc ctg cgc gaa ggt ttc cac gtt gtc acg    1728
Ala Asp Gln Tyr Ala Asp Phe Leu Arg Glu Gly Phe His Val Val Thr
                565                 570                 575 ccg aac aaa aag gcc aac acc tcg tcg atg gat tac tac cat cag ttg    1776
Pro Asn Lys Lys Ala Asn Thr Ser Ser Met Asp Tyr Tyr His Gln Leu
            580                 585                 590 cgt tat gcg gcg gaa aaa tcg cgg cgt aaa ttc ctc tat gac acc aac    1824
Arg Tyr Ala Ala Glu Lys Ser Arg Arg Lys Phe Leu Tyr Asp Thr Asn
        595                 600                 605 gtt ggg gct gga tta ccg gtt att gag aac ctg caa aat ctg ctc aat    1872
Val Gly Ala Gly Leu Pro Val Ile Glu Asn Leu Gln Asn Leu Leu Asn
610                 615                 620 gca ggt gat gaa ttg atg aag ttc tcc ggc att ctt tct ggt tcg ctt    1920
Ala Gly Asp Glu Leu Met Lys Phe Ser Gly Ile Leu Ser Gly Ser Leu
625                 630                 635                 640 tct tat atc ttc ggc aag tta gac gaa ggc atg agt ttc tcc gag gcg    1968
Ser Tyr Ile Phe Gly Lys Leu Asp Glu Gly Met Ser Phe Ser Glu Ala
                645                 650                 655 acc acg ctg gcg cgg gaa atg ggt tat acc gaa ccg gac ccg cga gat    2016
Thr Thr Leu Ala Arg Glu Met Gly Tyr Thr Glu Pro Asp Pro Arg Asp
            660                 665                 670 gat ctt tct ggt atg gat gtg gcg cgt aaa cta ttg att ctc gct cgt    2064
Asp Leu Ser Gly Met Asp Val Ala Arg Lys Leu Leu Ile Leu Ala Arg
        675                 680                 685 gaa acg gga cgt gaa ctg gag ctg gcg gat att gaa att gaa cct gtg    2112
Glu Thr Gly Arg Glu Leu Glu Leu Ala Asp Ile Glu Ile Glu Pro Val
690                 695                 700 ctg ccc gca gag ttt aac gcc gag ggt gat gtt gcc gct ttt atg gcg    2160
Leu Pro Ala Glu Phe Asn Ala Glu Gly Asp Val Ala Ala Phe Met Ala
705                 710                 715                 720 aat ctg tca caa ctc gac gat ctc ttt gcc gcg cgc gtg gcg aag gcc    2208
Asn Leu Ser Gln Leu Asp Asp Leu Phe Ala Ala Arg Val Ala Lys Ala
                725                 730                 735 cgt gat gaa gga aaa gtt ttg cgc tat gtt ggc aat att gat gaa gat    2256
Arg Asp Glu Gly Lys Val Leu Arg Tyr Val Gly Asn Ile Asp Glu Asp
            740                 745                 750 ggc gtc tgc cgc gtg aag att gcc gaa gtg gat ggt aat gat ccg ctg    2304
Gly Val Cys Arg Val Lys Ile Ala Glu Val Asp Gly Asn Asp Pro Leu
        755                 760                 765 ttc aaa gtg aaa aat ggc gaa aac gcc ctg gcc ttc tat agc cac tat    2352
Phe Lys Val Lys Asn Gly Glu Asn Ala Leu Ala Phe Tyr Ser His Tyr
770                 775                 780 tat cag ccg ctg ccg ttg gta ctg cgc gga tat ggt gcg ggc aat gac    2400
Tyr Gln Pro Leu Pro Leu Val Leu Arg Gly Tyr Gly Ala Gly Asn Asp
785                 790                 795                 800 gtt aca gct gcc ggt gtc ttt gct gat ctg cta cgt acc ctc tca tgg    2448
Val Thr Ala Ala Gly Val Phe Ala Asp Leu Leu Arg Thr Leu Ser Trp
                805                 810                 815 aag tta gga gtc tga                                                2463
Lys Leu Gly Val
            820
```

<210> SEQ ID NO 4
<211> LENGTH: 820
<212> TYPE: PRT
<213> ORGANISM: Escherichia coli

<400> SEQUENCE: 4

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
    130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
    210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
        275                 280                 285

Gln Ala Pro Gly Thr Leu Ile Gly Ala Ser Arg Asp Glu Asp Glu Leu
    290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu

```
                370                 375                 380
Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
                420                 425                 430

Gly Ser Ser Glu Arg Ser Ile Ser Val Val Asn Asn Asp Asp Ala
                435                 440                 445

Thr Thr Gly Val Arg Val Thr His Gln Met Leu Phe Asn Thr Asp Gln
                450                 455                 460

Val Ile Glu Val Phe Val Ile Gly Val Gly Val Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
                500                 505                 510

Val His Gly Leu Asn Leu Glu Asn Trp Gln Glu Leu Ala Gln Ala
                515                 520                 525

Lys Glu Pro Phe Asn Leu Gly Arg Leu Ile Arg Leu Val Lys Glu Tyr
                530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Thr
                565                 570                 575

Pro Asn Lys Lys Ala Asn Thr Ser Ser Met Asp Tyr Tyr His Gln Leu
                580                 585                 590

Arg Tyr Ala Ala Glu Lys Ser Arg Lys Phe Leu Tyr Asp Thr Asn
                595                 600                 605

Val Gly Ala Gly Leu Pro Val Ile Glu Asn Leu Gln Asn Leu Leu Asn
                610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655

Thr Thr Leu Ala Arg Glu Met Gly Tyr Thr Glu Pro Asp Pro Arg Asp
                660                 665                 670

Asp Leu Ser Gly Met Asp Val Ala Arg Lys Leu Leu Ile Leu Ala Arg
                675                 680                 685

Glu Thr Gly Arg Glu Leu Glu Leu Ala Asp Ile Glu Ile Glu Pro Val
                690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
                725                 730                 735

Arg Asp Glu Gly Lys Val Leu Arg Tyr Val Gly Asn Ile Asp Glu Asp
                740                 745                 750

Gly Val Cys Arg Val Lys Ile Ala Glu Val Asp Gly Asn Asp Pro Leu
                755                 760                 765

Phe Lys Val Lys Asn Gly Glu Asn Ala Leu Ala Phe Tyr Ser His Tyr
                770                 775                 780

Tyr Gln Pro Leu Pro Leu Val Leu Arg Gly Tyr Gly Ala Gly Asn Asp
785                 790                 795                 800
```

```
Val Thr Ala Ala Gly Val Phe Ala Asp Leu Leu Arg Thr Leu Ser Trp
            805                 810                 815

Lys Leu Gly Val
            820

<210> SEQ ID NO 5
<211> LENGTH: 2460
<212> TYPE: DNA
<213> ORGANISM: Serratia marcescens
<220> FEATURE:
<221> NAME/KEY: CDS
<222> LOCATION: (1)..(2460)
<223> OTHER INFORMATION: thrA coding region

<400> SEQUENCE: 5 atg cga gtg ctg aaa ttt ggc gga acc tcg gta gcg aat gcg gaa cgt        48
Met Arg Val Leu Lys Phe Gly Gly Thr Ser Val Ala Asn Ala Glu Arg
1               5                   10                  15 ttt ctg cgc gtc gcc gac atc atg gag agt aac gcg cgt cag gga cag        96
Phe Leu Arg Val Ala Asp Ile Met Glu Ser Asn Ala Arg Gln Gly Gln
                20                  25                  30 gta gcc acg gtc ttg tcc gcc ccc gca aag atc acc aac cat ctg gtg       144
Val Ala Thr Val Leu Ser Ala Pro Ala Lys Ile Thr Asn His Leu Val
            35                  40                  45 gcg atg atc gac aaa acg gtg gcg ggc cag gac att ctg ccg aat atg       192
Ala Met Ile Asp Lys Thr Val Ala Gly Gln Asp Ile Leu Pro Asn Met
        50                  55                  60 agc gac gcc gag cgg atc ttt gcc gac ctg ctg agc gga ctg gcg cag       240
Ser Asp Ala Glu Arg Ile Phe Ala Asp Leu Leu Ser Gly Leu Ala Gln
65                  70                  75                  80 gcg ctg ccg ggc ttt gaa tac gat cgt ttg aaa ggc gtg gtc gat cag       288
Ala Leu Pro Gly Phe Glu Tyr Asp Arg Leu Lys Gly Val Val Asp Gln
                85                  90                  95 gaa ttc gcg cag ctc aaa cag gtg ctg cat ggc gtc tcg ctg ctg ggg       336
Glu Phe Ala Gln Leu Lys Gln Val Leu His Gly Val Ser Leu Leu Gly
            100                 105                 110 cag tgc ccg gac agc gtg aac gcg gcg atc atc tgc cgt ggc gaa aag       384
Gln Cys Pro Asp Ser Val Asn Ala Ala Ile Ile Cys Arg Gly Glu Lys
        115                 120                 125 ctc tcc atc gcc atc atg gaa ggg gtg ttc cgc gcc aag ggt tat ccg       432
Leu Ser Ile Ala Ile Met Glu Gly Val Phe Arg Ala Lys Gly Tyr Pro
    130                 135                 140 gtc acg gtg atc aac ccg gtg gag aaa ctg ctg gcg cag ggc cac tac       480
Val Thr Val Ile Asn Pro Val Glu Lys Leu Leu Ala Gln Gly His Tyr
145                 150                 155                 160 ctg gag tcc acc gtg gac atc gcc gag tct acg ctg cgc atc gcc gcc       528
Leu Glu Ser Thr Val Asp Ile Ala Glu Ser Thr Leu Arg Ile Ala Ala
                165                 170                 175 gcg gcg atc ccg gcc gat cac atc gtg ctg atg gcc ggt ttc acc gcc       576
Ala Ala Ile Pro Ala Asp His Ile Val Leu Met Ala Gly Phe Thr Ala
            180                 185                 190 ggt aat gat aag ggc gag ctg gtg gtg ctg ggc cgc aac ggc tcc gac       624
Gly Asn Asp Lys Gly Glu Leu Val Val Leu Gly Arg Asn Gly Ser Asp
        195                 200                 205 tat tcc gcc gcg gtg ctg gcc gcc tgc ctg cgc gcc gac tgt tgc gag       672
Tyr Ser Ala Ala Val Leu Ala Ala Cys Leu Arg Ala Asp Cys Cys Glu
    210                 215                 220 atc tgg acc gac gtc gac ggc gtt tat acc tgc gat ccg cgc acc gtg       720
Ile Trp Thr Asp Val Asp Gly Val Tyr Thr Cys Asp Pro Arg Thr Val
225                 230                 235                 240
```

| | |
|---|---|
| ccg gac gcc agg tta ctg aaa tcg atg tcg tac cag gaa gcg atg gag<br>Pro Asp Ala Arg Leu Leu Lys Ser Met Ser Tyr Gln Glu Ala Met Glu<br>245 250 255 | 768 |
| ctt tcc tat ttc ggc gcc aaa gtg tta cac ccc cgc acc atc act ccg<br>Leu Ser Tyr Phe Gly Ala Lys Val Leu His Pro Arg Thr Ile Thr Pro<br>260 265 270 | 816 |
| att gcc cag ttt caa atc cct tgc ctg att aaa aac acc tcc aac ccg<br>Ile Ala Gln Phe Gln Ile Pro Cys Leu Ile Lys Asn Thr Ser Asn Pro<br>275 280 285 | 864 |
| cag gcc ccc ggc acg ctg atc ggc aaa gac agc acc gat gcc gat atg<br>Gln Ala Pro Gly Thr Leu Ile Gly Lys Asp Ser Thr Asp Ala Asp Met<br>290 295 300 | 912 |
| ccg gtg aag ggc atc acc aac ctg aac aac atg gcg atg atc aac gtc<br>Pro Val Lys Gly Ile Thr Asn Leu Asn Asn Met Ala Met Ile Asn Val<br>305 310 315 320 | 960 |
| tcc ggc ccg ggc atg aaa ggc atg gtc ggc atg gcc gca cgg gtc ttc<br>Ser Gly Pro Gly Met Lys Gly Met Val Gly Met Ala Ala Arg Val Phe<br>325 330 335 | 1008 |
| gcc gtg atg tcg cgc gcc ggc att tcg gtg gtg ctg atc acc caa tcc<br>Ala Val Met Ser Arg Ala Gly Ile Ser Val Val Leu Ile Thr Gln Ser<br>340 345 350 | 1056 |
| tct tcc gaa tac agc atc agc ttc tgc gtg ccg cag ggt gaa ctg cag<br>Ser Ser Glu Tyr Ser Ile Ser Phe Cys Val Pro Gln Gly Glu Leu Gln<br>355 360 365 | 1104 |
| cgc gcc cgt cgc gcg ctg gaa gag gag ttc tat ctg gag ctg aaa gac<br>Arg Ala Arg Arg Ala Leu Glu Glu Glu Phe Tyr Leu Glu Leu Lys Asp<br>370 375 380 | 1152 |
| ggc gtg ctg gat ccg ctg gac gtg atg gaa cgc ctg gcg atc atc tcg<br>Gly Val Leu Asp Pro Leu Asp Val Met Glu Arg Leu Ala Ile Ile Ser<br>385 390 395 400 | 1200 |
| gtg gtt ggc gac ggc atg cgc acc ctg cgc ggc att tcc gca cgc ttc<br>Val Val Gly Asp Gly Met Arg Thr Leu Arg Gly Ile Ser Ala Arg Phe<br>405 410 415 | 1248 |
| ttc tcc gcg ctg gcg cgc gcc aac atc aat atc gtt gcc atc gcc caa<br>Phe Ser Ala Leu Ala Arg Ala Asn Ile Asn Ile Val Ala Ile Ala Gln<br>420 425 430 | 1296 |
| ggg tct tcc gaa cgt tcc att tcg gtg gtg gtc agc aat gat tcc gcc<br>Gly Ser Ser Glu Arg Ser Ile Ser Val Val Val Ser Asn Asp Ser Ala<br>435 440 445 | 1344 |
| acc acc ggc gtg cgc gtc agc cac cag atg ctg ttc aac acc gat cag<br>Thr Thr Gly Val Arg Val Ser His Gln Met Leu Phe Asn Thr Asp Gln<br>450 455 460 | 1392 |
| gtg atc gaa gtg ttc gtc atc ggc gtc ggc ggc gtc ggc ggg gcg ctg<br>Val Ile Glu Val Phe Val Ile Gly Val Gly Gly Val Gly Gly Ala Leu<br>465 470 475 480 | 1440 |
| atc gag cag atc tat cgc cag cag ccg tgg ctg aag caa aaa cat atc<br>Ile Glu Gln Ile Tyr Arg Gln Gln Pro Trp Leu Lys Gln Lys His Ile<br>485 490 495 | 1488 |
| gat ctg cgg gtg tgc ggc atc gcc aac tcg cgc gtg atg ctg acc aat<br>Asp Leu Arg Val Cys Gly Ile Ala Asn Ser Arg Val Met Leu Thr Asn<br>500 505 510 | 1536 |
| gtg cac ggc atc gcg ctg gac agc tgg cgc gac gcg ctg gcc ggc gcg<br>Val His Gly Ile Ala Leu Asp Ser Trp Arg Asp Ala Leu Ala Gly Ala<br>515 520 525 | 1584 |
| cag gag ccg ttc aat ctc ggc cgt ctg atc cgg ctg gtg aag gaa tat<br>Gln Glu Pro Phe Asn Leu Gly Arg Leu Ile Arg Leu Val Lys Glu Tyr<br>530 535 540 | 1632 |
| cac ctg ctg aac ccg gtg atc gtc gac tgt acc tcc agt cag gcg gtg<br>His Leu Leu Asn Pro Val Ile Val Asp Cys Thr Ser Ser Gln Ala Val<br>545 550 555 560 | 1680 |

```
gcc gat cag tac gtg gac ttc ctg gcg gac ggc ttc cat gtg gtg acg      1728
Ala Asp Gln Tyr Val Asp Phe Leu Ala Asp Gly Phe His Val Val Thr
            565                 570                 575 ccg aac aaa aag gcc aac acc tcg tcg atg aac tat tat cag caa ctg      1776
Pro Asn Lys Lys Ala Asn Thr Ser Ser Met Asn Tyr Tyr Gln Gln Leu
        580                 585                 590 cgc gcg gcc gcc gcc ggt tcg cat cgc aag ttc ctg tac gac acc aac      1824
Arg Ala Ala Ala Ala Gly Ser His Arg Lys Phe Leu Tyr Asp Thr Asn
    595                 600                 605 gtc ggt gcc ggt ctg ccg gtg att gag aac ctg caa aac ctg ctg aac      1872
Val Gly Ala Gly Leu Pro Val Ile Glu Asn Leu Gln Asn Leu Leu Asn
610                 615                 620 gcc ggt gat gaa ctg gta cgt ttc tcc ggt atc ctg tcc ggc tcg ctg      1920
Ala Gly Asp Glu Leu Val Arg Phe Ser Gly Ile Leu Ser Gly Ser Leu
625                 630                 635                 640 tcc ttt atc ttc ggc aag ctg gac gaa ggg ctg tcg ctg tcg gcg gcg      1968
Ser Phe Ile Phe Gly Lys Leu Asp Glu Gly Leu Ser Leu Ser Ala Ala
                645                 650                 655 acc ctg cag gcc cgg gcc aac ggc tac acc gag ccg gat ccg cgc gac      2016
Thr Leu Gln Ala Arg Ala Asn Gly Tyr Thr Glu Pro Asp Pro Arg Asp
            660                 665                 670 gat ctg tcc ggg atg gat gtg gcg cgt aag ctg ctg atc ctg gcg cgc      2064
Asp Leu Ser Gly Met Asp Val Ala Arg Lys Leu Leu Ile Leu Ala Arg
        675                 680                 685 gag gcc ggt tac aaa ctg gaa ctg agc gat atc gag gtc gag ccg gtg      2112
Glu Ala Gly Tyr Lys Leu Glu Leu Ser Asp Ile Glu Val Glu Pro Val
    690                 695                 700 ctg ccg ccg tcc ttc gac gcg tcg ggc gac gtg gac acc ttc ctg gcg      2160
Leu Pro Pro Ser Phe Asp Ala Ser Gly Asp Val Asp Thr Phe Leu Ala
705                 710                 715                 720 cgg ttg ccg gag ctg gat aaa gag ttc gcg cgc aac gtg gct aac gcc      2208
Arg Leu Pro Glu Leu Asp Lys Glu Phe Ala Arg Asn Val Ala Asn Ala
                725                 730                 735 gcc gag caa ggc aag gtg ctg cgc tat gtc ggc ctg atc gac gaa ggg      2256
Ala Glu Gln Gly Lys Val Leu Arg Tyr Val Gly Leu Ile Asp Glu Gly
            740                 745                 750 cgc tgc aag gtg cgc att gag gcg gtg gac ggc aac gat ccg ttg tat      2304
Arg Cys Lys Val Arg Ile Glu Ala Val Asp Gly Asn Asp Pro Leu Tyr
        755                 760                 765 aaa gtg aag aac ggc gag aac gcg ctg gcc ttc tac agc cgc tac tat      2352
Lys Val Lys Asn Gly Glu Asn Ala Leu Ala Phe Tyr Ser Arg Tyr Tyr
    770                 775                 780 cag ccg ttg ccg ctg gtg ctg cgc ggc tac ggc gcc ggt aac gat gtg      2400
Gln Pro Leu Pro Leu Val Leu Arg Gly Tyr Gly Ala Gly Asn Asp Val
785                 790                 795                 800 act gca gcg ggc gta ttc gcc gat ctg ctg cgc aca ctg tca tgg aag      2448
Thr Ala Ala Gly Val Phe Ala Asp Leu Leu Arg Thr Leu Ser Trp Lys
                805                 810                 815 ttg gga gtt taa                                                      2460
Leu Gly Val <210> SEQ ID NO 6
<211> LENGTH: 819
<212> TYPE: PRT
<213> ORGANISM: Serratia marcescens

<400> SEQUENCE: 6

Met Arg Val Leu Lys Phe Gly Gly Thr Ser Val Ala Asn Ala Glu Arg
1               5                   10                  15
```

-continued

```
Phe Leu Arg Val Ala Asp Ile Met Glu Ser Asn Ala Arg Gln Gly Gln
             20                  25                  30

Val Ala Thr Val Leu Ser Ala Pro Ala Lys Ile Thr Asn His Leu Val
         35                  40                  45

Ala Met Ile Asp Lys Thr Val Ala Gly Gln Asp Ile Leu Pro Asn Met
 50                  55                  60

Ser Asp Ala Glu Arg Ile Phe Ala Asp Leu Leu Ser Gly Leu Ala Gln
 65                  70                  75                  80

Ala Leu Pro Gly Phe Glu Tyr Asp Arg Leu Lys Gly Val Val Asp Gln
                 85                  90                  95

Glu Phe Ala Gln Leu Lys Gln Val Leu His Gly Val Ser Leu Leu Gly
            100                 105                 110

Gln Cys Pro Asp Ser Val Asn Ala Ala Ile Ile Cys Arg Gly Glu Lys
        115                 120                 125

Leu Ser Ile Ala Ile Met Glu Gly Val Phe Arg Ala Lys Gly Tyr Pro
130                 135                 140

Val Thr Val Ile Asn Pro Val Glu Lys Leu Leu Ala Gln Gly His Tyr
145                 150                 155                 160

Leu Glu Ser Thr Val Asp Ile Ala Glu Ser Thr Leu Arg Ile Ala Ala
                165                 170                 175

Ala Ala Ile Pro Ala Asp His Ile Val Leu Met Ala Gly Phe Thr Ala
            180                 185                 190

Gly Asn Asp Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
210                 215                 220

Ile Trp Thr Asp Val Asp Gly Val Tyr Thr Cys Asp Pro Arg Thr Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Ser Asn Pro
        275                 280                 285

Gln Ala Pro Gly Thr Leu Ile Gly Lys Asp Ser Thr Asp Ala Asp Met
290                 295                 300

Pro Val Lys Gly Ile Thr Asn Leu Asn Asn Met Ala Met Ile Asn Val
305                 310                 315                 320

Ser Gly Pro Gly Met Lys Gly Met Val Gly Met Ala Ala Arg Val Phe
                325                 330                 335

Ala Val Met Ser Arg Ala Gly Ile Ser Val Val Leu Ile Thr Gln Ser
            340                 345                 350

Ser Ser Glu Tyr Ser Ile Ser Phe Cys Val Pro Gln Gly Glu Leu Gln
        355                 360                 365

Arg Ala Arg Arg Ala Leu Glu Glu Glu Phe Tyr Leu Glu Leu Lys Asp
370                 375                 380

Gly Val Leu Asp Pro Leu Asp Val Met Glu Arg Leu Ala Ile Ile Ser
385                 390                 395                 400

Val Val Gly Asp Gly Met Arg Thr Leu Arg Gly Ile Ser Ala Arg Phe
                405                 410                 415

Phe Ser Ala Leu Ala Arg Ala Asn Ile Asn Ile Val Ala Ile Ala Gln
            420                 425                 430

Gly Ser Ser Glu Arg Ser Ile Ser Val Val Val Ser Asn Asp Ser Ala
```

```
                435                 440                 445
Thr Thr Gly Val Arg Val Ser His Gln Met Leu Phe Asn Thr Asp Gln
450                 455                 460

Val Ile Glu Val Phe Val Ile Gly Val Gly Val Gly Gly Ala Leu
465                 470                 475                 480

Ile Glu Gln Ile Tyr Arg Gln Gln Pro Trp Leu Lys Gln Lys His Ile
                485                 490                 495

Asp Leu Arg Val Cys Gly Ile Ala Asn Ser Arg Val Met Leu Thr Asn
            500                 505                 510

Val His Gly Ile Ala Leu Asp Ser Trp Arg Asp Ala Leu Ala Gly Ala
        515                 520                 525

Gln Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Val Asp Phe Leu Ala Asp Gly Phe His Val Val Thr
                565                 570                 575

Pro Asn Lys Lys Ala Asn Thr Ser Ser Met Asn Tyr Tyr Gln Gln Leu
            580                 585                 590

Arg Ala Ala Ala Gly Ser His Arg Lys Phe Leu Tyr Asp Thr Asn
        595                 600                 605

Val Gly Ala Gly Leu Pro Val Ile Glu Asn Leu Gln Asn Leu Leu Asn
610                 615                 620

Ala Gly Asp Glu Leu Val Arg Phe Ser Gly Ile Leu Ser Gly Ser Leu
625                 630                 635                 640

Ser Phe Ile Phe Gly Lys Leu Asp Glu Gly Leu Ser Leu Ser Ala Ala
                645                 650                 655

Thr Leu Gln Ala Arg Ala Asn Gly Tyr Thr Glu Pro Asp Pro Arg Asp
            660                 665                 670

Asp Leu Ser Gly Met Asp Val Ala Arg Lys Leu Leu Ile Leu Ala Arg
        675                 680                 685

Glu Ala Gly Tyr Lys Leu Glu Leu Ser Asp Ile Glu Val Glu Pro Val
    690                 695                 700

Leu Pro Pro Ser Phe Asp Ala Ser Gly Asp Val Asp Thr Phe Leu Ala
705                 710                 715                 720

Arg Leu Pro Glu Leu Asp Lys Glu Phe Ala Arg Asn Val Ala Asn Ala
                725                 730                 735

Ala Glu Gln Gly Lys Val Leu Arg Tyr Val Gly Leu Ile Asp Glu Gly
            740                 745                 750

Arg Cys Lys Val Arg Ile Glu Ala Val Asp Gly Asn Asp Pro Leu Tyr
        755                 760                 765

Lys Val Lys Asn Gly Glu Asn Ala Leu Ala Phe Tyr Ser Arg Tyr Tyr
    770                 775                 780

Gln Pro Leu Pro Leu Val Leu Arg Gly Tyr Gly Ala Gly Asn Asp Val
785                 790                 795                 800

Thr Ala Ala Gly Val Phe Ala Asp Leu Leu Arg Thr Leu Ser Trp Lys
                805                 810                 815

Leu Gly Val

<210> SEQ ID NO 7
<211> LENGTH: 35
<212> TYPE: DNA
<213> ORGANISM: Escherichia coli
<220> FEATURE:
```

```
<221> NAME/KEY: -35_signal
<222> LOCATION: (1)..(6)
<220> FEATURE:
<221> NAME/KEY: -10_signal
<222> LOCATION: (24)..(30)
<220> FEATURE:
<221> NAME/KEY: start transcription
<222> LOCATION: (35)..(35)

<400> SEQUENCE: 7
tagtcagcag cataaaaaag tgccagtatg aagac                           35

<210> SEQ ID NO 8
<211> LENGTH: 35
<212> TYPE: DNA
<213> ORGANISM: Escherichia coli
<220> FEATURE:
<221> NAME/KEY: -35_signal
<222> LOCATION: (1)..(6)
<220> FEATURE:
<221> NAME/KEY: -10_signal
<222> LOCATION: (24)..(30)
<220> FEATURE:
<221> NAME/KEY: mutation
<222> LOCATION: (24)..(24)
<223> OTHER INFORMATION: transition  c -> t
<220> FEATURE:
<221> NAME/KEY: start transcription
<222> LOCATION: (35)..(35)

<400> SEQUENCE: 8
tagtcagcag cataaaaaag tgctagtatg aagac                           35

<210> SEQ ID NO 9
<211> LENGTH: 204
<212> TYPE: DNA
<213> ORGANISM: Escherichia coli
<220> FEATURE:
<221> NAME/KEY: -35_signal
<222> LOCATION: (139)..(144)
<220> FEATURE:
<221> NAME/KEY: -10_signal
<222> LOCATION: (162)..(168)
<220> FEATURE:
<221> NAME/KEY: start transcription
<222> LOCATION: (173)..(173)

<400> SEQUENCE: 9
attgagatgg ctgaacagat gccgatcacc gccagcgaaa tgctcagcgt taacggcgtt   60
gggatgcgca agctggaacg ctttggcaaa ccgtttatgg cgctgattcg tgcgcatgtt  120
gatggcgatg acgaagagta gtcagcagca taaaaaagtg ccagtatgaa gactccgtaa  180
acgtttcccc cgcgagtcaa atgt                                        204

<210> SEQ ID NO 10
<211> LENGTH: 1130
<212> TYPE: DNA
<213> ORGANISM: Escherichia coli
<220> FEATURE:
<221> NAME/KEY: CDS
<222> LOCATION: (205)..(825)
<223> OTHER INFORMATION: rhtC coding region

<400> SEQUENCE: 10
attgagatgg ctgaacagat gccgatcacc gccagcgaaa tgctcagcgt taacggcgtt   60
gggatgcgca agctggaacg ctttggcaaa ccgtttatgg cgctgattcg tgcgcatgtt  120
gatggcgatg acgaagagta gtcagcagca taaaaaagtg ccagtatgaa gactccgtaa  180
```

```
acgtttcccc cgcgagtcaa atgt atg ttg atg tta ttt ctc acc gtc gcc      231
                          Met Leu Met Leu Phe Leu Thr Val Ala
                           1               5 atg gtg cac att gtg gcg ctt atg agc ccc ggt ccc gat ttc ttt ttt     279
Met Val His Ile Val Ala Leu Met Ser Pro Gly Pro Asp Phe Phe Phe
 10              15                  20                  25 gtc tct cag acc gct gtc agt cgt tcc cgt aaa gaa gcg atg atg ggc     327
Val Ser Gln Thr Ala Val Ser Arg Ser Arg Lys Glu Ala Met Met Gly
             30                  35                  40 gtg ctg ggc att acc tgc ggc gta atg gtt tgg gct ggg att gcg ctg     375
Val Leu Gly Ile Thr Cys Gly Val Met Val Trp Ala Gly Ile Ala Leu
                 45                  50                  55 ctt ggc ctg cat ttg att atc gaa aaa atg gcc tgg ctg cat acg ctg     423
Leu Gly Leu His Leu Ile Ile Glu Lys Met Ala Trp Leu His Thr Leu
             60                  65                  70 att atg gtg ggc ggt ggc ctg tat ctc tgc tgg atg ggt tac cag atg     471
Ile Met Val Gly Gly Gly Leu Tyr Leu Cys Trp Met Gly Tyr Gln Met
 75                  80                  85 cta cgt ggt gca ctg aaa aaa gag gcg gtt tct gca cct gcg cca cag     519
Leu Arg Gly Ala Leu Lys Lys Glu Ala Val Ser Ala Pro Ala Pro Gln
 90                  95                 100                 105 gtc gag ctg gcg aaa agt ggg cgc agt ttc ctg aaa ggt tta ctg acc     567
Val Glu Leu Ala Lys Ser Gly Arg Ser Phe Leu Lys Gly Leu Leu Thr
                110                 115                 120 aat ctc gct aat ccg aaa gcg att atc tac ttt ggc tcg gtg ttc tca     615
Asn Leu Ala Asn Pro Lys Ala Ile Ile Tyr Phe Gly Ser Val Phe Ser
                125                 130                 135 ttg ttt gtc ggt gat aac gtt ggc act acc gcg cgc tgg ggc att ttt     663
Leu Phe Val Gly Asp Asn Val Gly Thr Thr Ala Arg Trp Gly Ile Phe
        140                 145                 150 gcg ctg atc att gtc gaa acg ctg gcg tgg ttt acc gtc gtt gcc agc     711
Ala Leu Ile Ile Val Glu Thr Leu Ala Trp Phe Thr Val Val Ala Ser
        155                 160                 165 ctg ttt gcc ctg ccg caa atg cgc cgt ggt tat caa cgt ctg gcg aag     759
Leu Phe Ala Leu Pro Gln Met Arg Arg Gly Tyr Gln Arg Leu Ala Lys
170                 175                 180                 185 tgg att gat ggt ttt gcc ggg gcg tta ttt gcc gga ttt ggc att cat     807
Trp Ile Asp Gly Phe Ala Gly Ala Leu Phe Ala Gly Phe Gly Ile His
                190                 195                 200 ttg att att tcg cgg tga tgccagacgc gtcttcagag taagtcggat            855
Leu Ile Ile Ser Arg
                205 aaggcgttta cgccgcatcc gacattattt ttcacgcatg cctcgccgat gctaacagcg   915 ctcccaccag cataaacaac gagccgaaaa tcttattcag cgccttcatc tgctttggtc   975 ctttaatcca tagagcaatc cgttgagcaa gggtggcgta accgatcatc acaataatat  1035 cgaccacaat agtggtgacg ccgagcacga tatactgcat cagttgcggc tgttgcggca  1095 tgatgaattg cggaaatagc gccgccagaa acaca                             1130

<210> SEQ ID NO 11
<211> LENGTH: 206
<212> TYPE: PRT
<213> ORGANISM: Escherichia coli

<400> SEQUENCE: 11

Met Leu Met Leu Phe Leu Thr Val Ala Met Val His Ile Val Ala Leu
 1               5                  10                  15

Met Ser Pro Gly Pro Asp Phe Phe Phe Val Ser Gln Thr Ala Val Ser
                 20                  25                  30
```

```
Arg Ser Arg Lys Glu Ala Met Met Gly Val Leu Gly Ile Thr Cys Gly
         35                  40                  45

Val Met Val Trp Ala Gly Ile Ala Leu Leu Gly Leu His Leu Ile Ile
 50                  55                  60

Glu Lys Met Ala Trp Leu His Thr Leu Ile Met Val Gly Gly Gly Leu
 65                  70                  75                  80

Tyr Leu Cys Trp Met Gly Tyr Gln Met Leu Arg Gly Ala Leu Lys Lys
                 85                  90                  95

Glu Ala Val Ser Ala Pro Ala Pro Gln Val Glu Leu Ala Lys Ser Gly
                100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

<210> SEQ ID NO 12
<211> LENGTH: 800
<212> TYPE: DNA
<213> ORGANISM: Escherichia coli
<220> FEATURE:
<221> NAME/KEY: gene
<222> LOCATION: (92)..(712)
<223> OTHER INFORMATION: rhtC coding region
<220> FEATURE:
<221> NAME/KEY: CDS
<222> LOCATION: (92)..(712)

<400> SEQUENCE: 12
gcatgttgat ggcgatgacg aagagtagtc agcagcataa aaaagtgcta gtatgaagac    60
tccgtaaacg tttccccccgc gagtcaaatg t atg ttg atg tta ttt ctc acc    112
                                   Met Leu Met Leu Phe Leu Thr
                                    1               5 gtc gcc atg gtg cac att gtg gcg ctt atg agc ccc ggt ccc gat ttc    160
Val Ala Met Val His Ile Val Ala Leu Met Ser Pro Gly Pro Asp Phe
         10                  15                  20 ttt ttt gtc tct cag acc gct gtc agt cgt tcc cgt aaa gaa gcg atg    208
Phe Phe Val Ser Gln Thr Ala Val Ser Arg Ser Arg Lys Glu Ala Met
 25                  30                  35 atg ggc gtg ctg ggc att acc tgc ggc gta atg gtt tgg gct ggg att    256
Met Gly Val Leu Gly Ile Thr Cys Gly Val Met Val Trp Ala Gly Ile
 40                  45                  50                  55 gcg ctg ctt ggc ctg cat ttg att atc gaa aaa atg gcc tgg ctg cat    304
Ala Leu Leu Gly Leu His Leu Ile Ile Glu Lys Met Ala Trp Leu His
                 60                  65                  70 acg ctg att atg gtg ggc ggt ggc ctg tat ctc tgc tgg atg ggt tac    352
Thr Leu Ile Met Val Gly Gly Gly Leu Tyr Leu Cys Trp Met Gly Tyr
             75                  80                  85 cag atg cta cgt ggt gca ctg aaa aaa gag gcg gtt tct gca cct gcg    400
Gln Met Leu Arg Gly Ala Leu Lys Lys Glu Ala Val Ser Ala Pro Ala
         90                  95                 100
```

```
cca cag gtc gag ctg gcg aaa agt ggg cgc agt ttc ctg aaa ggt tta        448
Pro Gln Val Glu Leu Ala Lys Ser Gly Arg Ser Phe Leu Lys Gly Leu
        105                 110                 115 ctg acc aat ctc gct aat ccg aaa gcg att atc tac ttt ggc tcg gtg        496
Leu Thr Asn Leu Ala Asn Pro Lys Ala Ile Ile Tyr Phe Gly Ser Val
120                 125                 130                 135 ttc tca ttg ttt gtc ggt gat aac gtt ggc act acc gcg cgc tgg ggc        544
Phe Ser Leu Phe Val Gly Asp Asn Val Gly Thr Thr Ala Arg Trp Gly
                140                 145                 150 att ttt gcg ctg atc att gtc gaa acg ctg gcg tgg ttt acc gtc gtt        592
Ile Phe Ala Leu Ile Ile Val Glu Thr Leu Ala Trp Phe Thr Val Val
                155                 160                 165 gcc agc ctg ttt gcc ctg ccg caa atg cgc cgt ggt tat caa cgt ctg        640
Ala Ser Leu Phe Ala Leu Pro Gln Met Arg Arg Gly Tyr Gln Arg Leu
                170                 175                 180 gcg aag tgg att gat ggt ttt gcc ggg gcg tta ttt gcc gga ttt ggc        688
Ala Lys Trp Ile Asp Gly Phe Ala Gly Ala Leu Phe Ala Gly Phe Gly
        185                 190                 195 att cat ttg att att tcg cgg tga tgccagacgc gtcttcagag taagtcggat       742
Ile His Leu Ile Ile Ser Arg
200                 205 aaggcgttta cgccgcatcc gacattattt ttcacgcatg cctcgccgat gctaacag        800

<210> SEQ ID NO 13
<211> LENGTH: 206
<212> TYPE: PRT
<213> ORGANISM: Escherichia coli

<400> SEQUENCE: 13

Met Leu Met Leu Phe Leu Thr Val Ala Met Val His Ile Val Ala Leu
1               5                   10                  15

Met Ser Pro Gly Pro Asp Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Leu Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
        115                 120                 125

Ile Ile Tyr Phe Gly Ser Val Phe Ser Leu Phe Val Gly Asp Asn Val
    130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

<210> SEQ ID NO 14
```

```
<211> LENGTH: 1412
<212> TYPE: DNA
<213> ORGANISM: Escherichia coli
<220> FEATURE:
<221> NAME/KEY: mutation
<222> LOCATION: (806)..(806)
<223> OTHER INFORMATION: rhtC promoter mutation, C to T
<220> FEATURE:
<221> NAME/KEY: gene
<222> LOCATION: (849)..(1412)
<223> OTHER INFORMATION: 5 prime region coding sequence rhtC

<400> SEQUENCE: 14
gccgttgtct ggaagagaag ccgcaggggc agttgcagga tatcgagcgc cacaaactca      60
atgcgatggg cgcgtttgcc gaagcgcaaa cttgccgtcg tctggtattg ctgaactatt     120
ttggcgaagg gcgtcaggag ccgtgcggga actgcgatat ctgcctcgat ccgccgaaac     180
agtacgacgg ttcaaccgat gctcagattg ccctttccac cattggtcgt gtgaatcagc     240
ggtttgggat gggttatgtg gtggaagtga ttcgtggtgc taataaccag cgtatccgcg     300
actatggtca tgacaaactg aaagtctatg gcatgggccg tgataaaagc catgaacatt     360
gggtgagcgt gatccgccag ctgattcacc tcggcctggt gacgcaaaat attgcccagc     420
attctgccct acaactgaca gaggccgcgc gcccggtgct gcgcggcgaa tcctctttgc     480
aacttgccgt gccgcgtatc gtggcgctca aaccgaaagc gatgcagaaa tcgttcggcg     540
gcaactatga tcgcaaactg ttcgccaaat tacgcaaact gcgtaaatcg atagccgatg     600
aaagtaatgt cccgccgtac gtggtgttta acgacgcaac cttgattgag atggctgaac     660
agatgccgat caccgccagc gaaatgctca gcgtcaacgg cgttgggatg cgcaagctgg     720
aacgctttgg caaaccgttt atggcgctga ttcgtgcgca tgttgatggc gatgacgaag     780
agtagtcagc agcataaaaa agtgctagta tgaagactcc gtaaacgttt cccccgcgag     840
tcaaatgtat gttgatgtta tttctcaccg tcgccatggt gcacattgtg gcgcttatga     900
gccccggtcc cgatttcttt tttgtctctc agaccgctgt cagtcgttcc cgtaaagaag     960
cgatgatggg cgtgctgggc attacctgcg gcgtaatggt ttgggctggg attgcgctgc    1020
ttggcctgca tttgattatc gaaaaaatgg cctggctgca tacgctgatt atggtgggcg    1080
gtggcctgta tctctgctgg atgggttacc agatgctacg tggtgcactg aaaaaagagg    1140
cggtttctgc acctgcgcca caggtcgagc tggcgaaaag tgggcgcagt ttcctgaaag    1200
gtttactgac caatctcgct aatccgaaag cgattatcta ctttggctcg gtgttctcat    1260
tgtttgtcgg tgataacgtt ggcactaccg cgcgctgggg cattttttgcg ctgatcattg    1320
tcgaaacgct ggcgtggttt accgtcgttg ccagcctgtt tgccctgccg caaatgcgcc    1380
gtggttatca acgtctggcg aagtggattg at                                  1412

<210> SEQ ID NO 15
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: primer Tdh1

<400> SEQUENCE: 15
tcgcgaccta taagtttggg                                                  20

<210> SEQ ID NO 16
<211> LENGTH: 20
```

```
<212> TYPE: DNA
<213> ORGANISM: Escherichia coli
<220> FEATURE:
<221> NAME/KEY: misc_feature
<222> LOCATION: (1)..(20)
<223> OTHER INFORMATION: primer Tdh2

<400> SEQUENCE: 16
aataccagcc cttgttcgtg                                                      20

<210> SEQ ID NO 17
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: primer PrhtC-1

<400> SEQUENCE: 17
gcatgttgat ggcgatgacg                                                      20

<210> SEQ ID NO 18
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: primer PrhtC-2

<400> SEQUENCE: 18
ctgttagcat cggcgaggca                                                      20

<210> SEQ ID NO 19
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: primer reqQ_1

<400> SEQUENCE: 19
gccgttgtct ggaagagaag                                                      20

<210> SEQ ID NO 20
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: primer rht1r

<400> SEQUENCE: 20
atcaatccac ttcgccagac                                                      20

<210> SEQ ID NO 21
<211> LENGTH: 21
<212> TYPE: DNA
<213> ORGANISM: Artificial Sequence
<220> FEATURE:
<223> OTHER INFORMATION: PKO3-L primer

<400> SEQUENCE: 21
agggcagggt cgttaaatag c                                                    21
```

```
<210> SEQ ID NO 22
<211> LENGTH: 21
<212> TYPE: DNA
<213> ORGANISM: Artificial Sequence
<220> FEATURE:
<223> OTHER INFORMATION: PKO3-R primer

<400> SEQUENCE: 22
ttaatgcgcc gctacagggc g                                           21
```